United States Patent
Ott

(10) Patent No.: US 10,758,498 B2
(45) Date of Patent: Sep. 1, 2020

(54) METHOD OF DECREASING PROTEIN-ALDEHYDE ADDUCTS BY ADMINISTERING A MIXED DISULFIDE OF N-ACETYLCYSTEINE AND PROPYL MERCAPTAN, PROPENYL MERCAPTAN, OR ALLYL MERCAPTAN

(71) Applicant: David Michael Ott, Oakland, CA (US)

(72) Inventor: David Michael Ott, Oakland, CA (US)

( * ) Notice: Subject to any disclaimer, the term of this patent is extended or adjusted under 35 U.S.C. 154(b) by 39 days.

(21) Appl. No.: 16/186,077

(22) Filed: Nov. 9, 2018

(65) Prior Publication Data

US 2019/0076377 A1 Mar. 14, 2019

Related U.S. Application Data

(60) Division of application No. 15/387,181, filed on Dec. 21, 2016, now Pat. No. 10,258,581, which is a division of application No. 13/694,447, filed on Dec. 3, 2012, now Pat. No. 9,562,007, which is a
(Continued)

(51) Int. Cl.
| | |
|---|---|
| *A61K 31/10* | (2006.01) |
| *C07C 323/59* | (2006.01) |
| *C07C 319/24* | (2006.01) |
| *A23L 33/10* | (2016.01) |
| *A61K 31/198* | (2006.01) |
| *A61K 47/54* | (2017.01) |

(Continued)

(52) U.S. Cl.
CPC .............. *A61K 31/10* (2013.01); *A23L 33/10* (2016.08); *A61K 9/48* (2013.01); *A61K 31/198* (2013.01); *A61K 47/542* (2017.08); *C07C 319/24* (2013.01); *C07C 323/59* (2013.01); *A61K 33/06* (2013.01)

(58) Field of Classification Search
None
See application file for complete search history.

(56) References Cited

U.S. PATENT DOCUMENTS

| 7,678,833 B2 | 3/2010 | Ott |
| 8,217,084 B2 | 7/2012 | Ott |

(Continued)

FOREIGN PATENT DOCUMENTS

| EP | 2139465 B1 | 9/2012 |
| JP | 62063517 | 9/2012 |
| WO | 2008135984 A1 | 11/2008 |

OTHER PUBLICATIONS

Wood-Kaczmar et al. Understanding th molecular causes of Parkinson's disease. TRENDS in Molecular Medicine, vol. 12, No. 11, 2006.*

(Continued)

*Primary Examiner* — Anna Pagonakis

(57) ABSTRACT

Divalent salts of S-allylmercapto-N-acetylcysteine and related compositions are disclosed which can be administered in order to provide protection from the formation of aldehyde-protein adducts, protein carbonylation, protein aggregation, and the resulting neuroinflammation. Various neurodegenerative diseases which are suitable for treatment using these compositions include Alzheimer's disease, senile dementia, Parkinson's disease, multiple sclerosis, Lewy body disease, peripheral neuropathy, spinal cord injury, stroke and cerebral ischemia.

14 Claims, 10 Drawing Sheets

Acrolein

Allicin

Related U.S. Application Data continuation-in-part of application No. 13/373,878, filed on Dec. 5, 2011, now Pat. No. 9,456,999.

(51) Int. Cl.
  *A61K 9/48* (2006.01)
  *A61K 33/06* (2006.01)

(56) References Cited

U.S. PATENT DOCUMENTS

| | | |
|---|---|---|
| 8,455,552 B2 | 6/2013 | Savion |
| 2013/0143967 A1 | 6/2013 | Ott |

OTHER PUBLICATIONS

Quarles RH, et al. Myelin Formation, Structure and Biochemistry. In: Siegel GJ, Agranoff BW, Albers RW, et al., ?.. ditors. Basic Neurochemistry: Molecular, Cellular and Medical Aspects. 6th edition. Philadelphia: Lippincott-Raven; 1999. Chapter 4.
Cygan, Adduction of Cholesterol 5,6-Secosterol Aldehyde to Membrane-Bound Myelin Basic Protein Exposes an mmunodominant Epitope, Biochemistry, 2011, pp. 2092-2100, vol. 50.
Eung, Anti-Acrolein Treatment Improves Behavioral Outcome and Alleviates Myelin Damage in Experimental Autoimmune Enchephalomyelitis Mouse, Neuroscience, 2011, pp. 150-155, vol. 173.
Hamilton, Elevated Protein Carbonyloation, and Misfolding in Sciatic Nerve from dbldb and Soc1-/- Mice: Plausible ink between Oxidative Stress and Demyelination, Jun. 2013, 10 pgs, vol. 8, Issue 6.
Nie, Amyloid-like aggregates of neuronal tau induced by formaldehyde promote apoptosis of neuronal cells, BMC Neuroscience, Jan. 23, 2007, 16 pgs.
Potential implications of endogenous aldehydes in B-amyloid misfolding, oligomerization and fibrillogenesis, Journal of Neurochemistry, 2006, pp. 1413-1424, vol. 99.
Venere, Findings suggest new cause, possible treatment for multiple sclerosis, Nov. 23, 2010, 3 pgs, downloaded from: http://www.purdue_edu/newsroom/research/2010/101123ShiAcrolein_html.
Anderson, et al. Glutathione monoethyl ester: preparation, uptake by tissues, and conversion to glutathione; Archives of Biochemistry and Biophysics, 1985, pp. 538-548, vol. 239, No. 2.
Di Buono et al., Total sulfur amino acid requirement in young men as determined by indicator amino acid oxidation; American Journal of Clinical Nutrition, 2001, pp. 756-760, vol. 74, No. 6.
Meister, Glutathione; Anual Review of Biochemistry, 1983, pp. 711-760, vol. 52.
Zuo et al., Variation in APOE and STH loci and Alzheimer's disease; Behavioral and Brain Functions, 2005, pp. 13, vol. 2.
Gyamlan I et al., Acetaminophen toxicity: suicidal vs accidental; Critical Care, 2002, pp. 155, vol. 6.
Neuhouser et al., Fruits and Vegetables Are Associated with Lower Lung Cancer Risk Only in the Placebo Arm of the β-Carotene and Retinol Efficacy Trial (CARET); Cancer Epidemiology; Biomarkers & Prevention, 2003, pp. 350-358, vol. 12, No. 4.
Bahlis et al., Feasibility and Correlates of Arsenic Trioxide Combined with Ascorbic Acid-mediated Depletion of Intracellular Glutathione for the Treatment of Relapsed/Refractory Multiple Myeloma; Clinical Cancer Research, 2002, pp. 3658-3668, vol. 8, No. 2.
Xu et al., Structural Characterization of a 4-Hydroxy-2-alkenal-Derived Fluorophore That Contributes to Lipoperoxidation-Dependent Protein Cross-Linking in Aging and Degenerative Disease; Chemical Research in Toxicology, 1998, pp. 247-251, vol. 11, No. 4.
Gao et al., Neuroinflammation and α-Synuclein Dysfunction Potentiate Each Other, Driving Chronic Progression of Neurodegeneration in a Mouse Model of Parkinson's Disease; Environmental Health Perspectives, 2011, pp. 807-814, vol. 119, No. 6.
Abdul et al., Oxidative damage in brain from human mutant APP/PS-1 double knock-in mice as a function of age; Free Radicals in Biology and Medicine, 2008, pp. 1420-1425-. vol. 45, No. 10.
Izgov et al., S-allylmercapto-N-acetylcysteine up-regulates cellular glutathione and protects vascular endothelial cells from oxidative stress; Free Radicals in Biology and Medicine, 2011, pp. 1131-1139, vol. 50, No. 9.
Akama et al., Beta-amyloid stimulation of inducible nitric-oxide synthase in astrocytes is interleukin-1beta- and tumor necrosis factor-alpha (TNFalpha)-dependent, and involves a TNFalpha receptor-associated factor- and NFkappaB-inducing kinase-dependent signaling mechanism; Journal of Biological Chemistry, 2000, pp. 7918-7924, vol. 75, No. 11.
Choi et al., Oxidative modifications and down-regulation of ubiquitin carboxyl-terminal hydrolase L1 associated with idiopathic Parkinson's and Alzheimer's diseases; Journal of Biological Chemistry, 2004, pp. 13256, vol. 279, No. 13.
Zhou et al., DJ-1 up-regulates glutathione synthesis during oxidative stress and inhibits A53T alpha-synuclein toxicity; Journal of Biological Chemistry, 2005, pp. 43150-43158, vol. 280.
Qin et al., Effect of 4-hydroxy-2-nonenal modification on alpha synuclein aggregation; Journal of Biological Chemistry, 2007, pp. 5862-5870, vol. 282, No. 8.
Sugaya et al., New anti-inflammatory treatment stretegy in Alzheimer's disease; Japanese Journal of Pharmacology, 2000, pp. 85-94, vol. 82, No. 2.
Halle et al., The NALP3 inflammasome is involved in the innate immune response to amyloid-beta; Nature Immunology, 2008, pp. 857-865, vol. 9, No. 8.
Butterfield et al., Evidence that amyloid beta-peptide-induced lipid peroxidation and its sequeale in Alzheimer's disease brain contribute to neuronal death; Neurobiology of Aging, 2002, pp. 655-664, vol. 23, No. 5.
Pocernich et al., Glutathione elevation and its protective role in acrolein-induced protein damage in synaptosomal membranes: relevance to brain lipid peroxidation in neurodegenerative disease; Neurochemistry International; 2001, pp. 141-149, vol. 39, No. 2.
Leung et al., Anti-acrolein treatment improves behavioral outcome and alleviates myelin damage in experimental autoimmune encephalomyelitis mouse; Neuroscuence, 2011, pp. 150-155, vol. 173.
O'Mullan et al. Sniffing out the truth; New York Times Jan. 21, 2007.
Turin, What you can't smell will kill you; New York Times Jan. 21, 2007.
Rakovac et al., Mutations in PINK1 andParkin impair ubiquination of Mitofusins in human fibroblasts; PLoS ONE, 2011, 6:E16746.
Schmechl et al., Increased amyloid beta-peptide deposition in cerebral cortex as a consequence of apolipoprotein E.; Proceedings of the National Academy of Sciences, 1993, pp. 9649-9653, vol. 90, No. 20.
Block, Garlic and other Alliums; p. 150; RSC Publishing, Cambridge UK, 2010.
Vermeulen et al., Glutathione S-Transferases; pp. 199-211; Taylor and Francis Ltd, London, 1996.
Schauenstein et al., Aldehydes in Biological Systems; pp. 66-69; Pion Limited, London, 1977.
Cadenas et al., Handbook of Antioxidants; pp. 235-249; Marcel Decker, NY, 2001.
Koch et al., Garlic; pp. 42 and 93; Williams & Wilkins, Baltimore, MD, 1996.

\* cited by examiner

Acrolein

Allicin

Allyl Mercaptan

Diallyl disulfide 4-hydroxy-2-nonenal (HNE)

N-acetylcysteine

Propyl Mercaptan

S-allylmercapto-N-acetylcysteine

Protein-HNE Michael Adduct Formation

Protein Repair and Allyl Mercaptan-HNE Adduct Formation

Protein-HNE Schiff Base Formation

Irreversible Protein-Protein Cross-Link Formation

S-allylmercapto-N-acetylcysteine Sodium salt

S-propylmercapto-N-acetylcysteine Potassium salt

2 SAMNAC + Mg salt

2 SPMNAC + Mg salt

METHOD OF DECREASING PROTEIN-ALDEHYDE ADDUCTS BY ADMINISTERING A MIXED DISULFIDE OF N-ACETYLCYSTEINE AND PROPYL MERCAPTAN, PROPENYL MERCAPTAN, OR ALLYL MERCAPTAN

This application is a divisional application of U.S. application Ser. No. 15/387,181, filed Dec. 21, 2016, which is a divisional application of U.S. application Ser. No. 13/694,447, filed Dec. 3, 2012, which is a continuation in part of U.S. application Ser. No. 13/373,878, filed on Dec. 5, 2011, each of which is hereby incorporated by reference in its entirety.

FIELD OF THE INVENTION

The invention relates to organosulfur compounds that can be used to prevent or treat neurodegenerative diseases. More specifically, a class of lipophilic mercaptans are disclosed which can be used to decrease the formation of aldehyde-protein adducts, protein carbonylation, protein aggregates, and the resulting neuroinflammation. Examples of use include the treatment of diseases and conditions such as Alzheimer's disease, senile dementia, Parkinson's disease, multiple sclerosis, Lewy body disease, peripheral neuropathy, spinal cord injury, stroke and cerebral ischemia.

BACKGROUND OF THE INVENTION

1. Definitions, Glossary, and Abbreviations

Note: Unless otherwise stated, all amino acids mentioned within the specification or the claims are of the L-isomer.

Acrolien: The smallest and most reactive alpha,beta-unsaturated aldehyde; chemical formula (see also FIG. 1A):

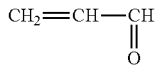

Administration of a compound: Causing a compound to enter into the body of an animal, either orally, by injection, or by any other means.

Allicin; (diallyl thiosulfinate): The principal thiosulfinate that is formed when garlic is crushed; chemical formula (also see FIG. 1B):

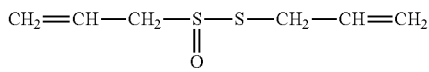

Allyl mercaptan; (also represented chemically as AllylSH), chemical name AllylThiol; chemical formula (also see FIG. 1C):

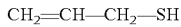

In the present exposition allyl mercaptan is the model lipophilic mercaptan (preferring a lipid environment to an aqueous environment). In general, a compound is referred to herein as a "model" compound when it is representative of a more general class of compounds defined herein.

Allylmercapto radical: allyl mercaptan without the terminal hydrogen atom of the SH group, resulting in an unpaired electron on the sulfur atom which is available for covalent bonding to the remainder of a larger molecule; chemical formula:

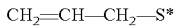

Amphiphilic molecule: A molecule having a more polar, water-soluble group attached to a less polar, lipid-soluble organic group.

Biothiol: Any thiol that is commonly found in biological systems. Common biothiols are cysteine, glutathione, several types of antioxidants (such as the dithiol form of lipoic acid), and several types of vitamins (such as the thiol form of thiamine).

Diallyl Disulfide; DADS, (also represented chemically as AllylSSAllyl or ASSA): the disulfide formed from two AllylMercapto radicals bonded together. Equivalent to deoxygenated allicin. In the present exposition diallyl disulfide is the model disulfide compound. See also FIG. 1D.

Glutathione: A tripeptide composed of the amino acids glutamate, cysteine, and glycine (ARB52:711). Glutathione is present in biological systems in a variety of forms, the most important of which are reduced glutathione (GSH), the anion of reduced glutathione (GS$^-$), the glutathiyl free radical (GS*), glutathione disulfide (GSSG), mixed glutathione disulfides (GSSR), and protein-glutathione mixed disulfides (PSSG).

The term "glutathione" used by itself can be used to refer to the sum of GSH and GS$^-$. The term "oxidized glutathione" usually refers to GSSG (the typical end product of oxidation, even though GS* is usually the initial oxidation product). The term "total glutathione" refers to the sum of all of these.

4-hydroxy-2-nonenal; 4-HNE, HNE: An alpha,beta-unsaturated aldehyde that has been extensively researched. See also FIG. 1E.

Lipophilic molecule: Attracted to lipids. A molecule is lipophilic if it preferentially partitions into the oily side of an oil and water system. For example, allyl mercaptan has a partition coefficient (Log P) of 1.51, which indicates that its concentration on the oily side is approximately 30 times its concentration on the aqueous side of an oil and water system.

Metabolism: The entire set of chemical reactions that can occur within a living organism. This includes anabolism (the formation of more complex molecules from simple ones), catabolism (the break down of complex molecules from complex molecules to make simpler ones) and also simpler reactions, such as thiol-disulfide exchange reactions.

Mercaptan: A small molecule with the general formula RSH where R is any radical. Mercaptans are the subset of thiols which are small molecules and only have one terminal sulfhydryl (SH). Mercaptans are typically volatile and very smelly.

Mitigate: To make less severe or less intense.

Molecular Mass: The mass of a molecule expressed in units of 1/12 of the weight of one atom of the isotope carbon-12.

Neuropathy: A disease or abnormality of the nervous system.

Nutraceutical: A food to which a substance has been added to promote health.

Prodrug: An inert drug that becomes active only after it is transformed or metabolized by the body.

Prophylactic treatment: Acting to defend against or prevent a disease.

Propyl mercaptan; n-Propyl Mercaptan, PropylSH, chemical name 1-PropaneThiol; chemical formula:

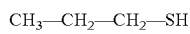

Protein-aldehyde adduct: a protein that has been modified by the attachment of an aldehyde.

Protein carbonylation: The net addition of a carbonyl group onto a protein, including protein carbonyls that are formed by the addition of an aldehyde.

Radical; R: A group of atoms which behaves as a unit and has one or more unpaired electrons.

Reactive Oxygen Species; ROS: oxygen containing molecules that are capable of producing oxidative damage to other molecules. Many, but not all, ROS are free radicals. Examples include: $H_2O_2$ (hydrogen peroxide), $*O_2^-$ (superoxide radical), $*OH$ (hydroxyl radical), $HOCl$ (hypoclorus acid), $ONOO^-$ (peroxynitrite), $O_2^1$ (singlet oxygen), $O_3$ (ozone), $*NO$ (nitric oxide), and $*NO_2$ (nitrogen dioxide).

S-allylmercapto-N-acetylcysteine; SAMNAC: The mixed disulfide formed from allyl mercaptan and N-acetylcysteine; chemical formula (see also FIG. 1H):

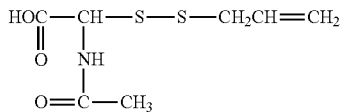

S-propylmercapto-N-acetylcysteine; SPMNAC: The mixed disulfide formed from propyl mercaptan and N-acetylcysteine; chemical formula:

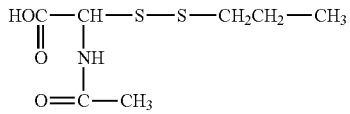

Sulfur Amino Acids; SAA: typically the sum of cysteine, cystine, methionine (constituents of proteins), and other sulfur containing amino acid molecules such as homocysteine, cysteamine, and N-acetylcysteine. Because they are amino acids (which are zwitterons with ionized amino and carboxyl groups), these molecules are too polar to be able to freely diffuse through biological membranes.

Thiol: Any molecule that includes one or more terminal sulfhydryl (SH). Mercaptans (RSH) are the subset of thiols which are small molecules and only have one terminal sulfhydryl (SH).

Trans-adduction: The transfer of an adduct from one molecule to another. For example, the transfer of a protein-aldehyde adduct from a protein molecule to a mercaptan molecule, repairing the protein and forming a mercaptan-aldehyde conjugate molecule.

Treatment: The willful administration of a therapeutic agent with the intent of preventing or mitigating a disease or an abnormal condition.

2. References

For articles contained in books, the first listing (typically by Dewey decimal number or ISBN number) contains identification information for the book and the actual reference(s) are the listings for the article(s) or pages that follow.

ABB239:538; M. E. Anderson et al; Glutathione Monoethyl Ester: Preparation, Uptake by Tissues, and Conversion to Glutathione; Archives of Biochemistry and Biophysics 239:538.

AJCN74:756; M. Buono et al; Total Sulfur Amino Acid Requirement in Young Men as Determined by Indicator Amino Acid Oxidation; American Journal of Clinical Nutrition 74:756.

ARB52:711; A. Meister and M. Anderson; Glutathione; Annual Review of Biochemistry 52:711.

BMCBBF2:13; L. Zuo et al; Variation at APOE and STH loci and Alzheimer's disease; BioMed Central Behavioral and Brain Function 2:13.

BMCCC6:155; G. G. Gyamlani et al; Acetaminophen toxicity: suicidal vs accidental; BioMed Central Critical Care 6:155.

CBEP12:350; M. L. Neuhouser et al; Fruits and Vegetables Are Associated with Lower Lung Cancer Risk Only in the Placebo Arm of the beta-Carotene and Retinol Efficacy Trial (CARET); Cancer Epidemiology, Biomarkers & Prevention 12:350.

CCR8:3658; N. Bahlis et al; Feasibility and Correltaes of Arsenic Trioxide Combined with Ascorbic Acid-mediated Depletion of Intrecellular Glutathone for the Treatment of Relapsed/Refractory Multiple Myeloma; Clinical Cancer Research 8:3658.

CRT11:247; G. Xu et al; Structural Characterization of a 4-Hydroxy-2-alkenal-Derived Fluorophore That Contributes to Lipoperoxidation-Dependent Protein Cross-Linking in Aging and Degenerative Disease; Chemical Research in Toxicology 11:247.

EHP119:867; Neuroinflammation and alpha-synuclein dysfunction potentiate each other, driving chronic progression of neurodegeneration in a mouse model of Parkinson's disease; H. Gao et al; Environmental Health Perspectives 119:807.

FRBM45:1420; H. A. Abdul et al; Oxidative damage in brain from human mutant APP/PS-1 double knock-in mice as a function of age; Free Radicals in Biology and Medicine 45:1420.

JALHZD4:193; D. A. Butterfield et al; Amyloid beta-peptide and amyloid pathology are central to the oxidative stress and inflammatory cascades under which Alzheimer's disease brain exists; Journal of Alzheimer's Disease 4:193.

JBC275:7918; K. T. Akama et al; beta-Amyloid Stimulation of Inducible Nitric-oxide Synthase in Astrocytes is Interleukin-1 beta and Tumor Necrosis Factor-alpha dependent, and involves TNFalpha Receptor-associated Factor- and NFkB-inducing Kinase-dependent Signaling Mechanism; Journal of Biological Chemistry 275:7918.

JBC279:13256; J. Choi et al; Oxidative Modifications and Down-regulation of Ubiquitin Carbonyl-terminal Hydrolase L1 Associated with Idopathic Parkinson's and Alzheimer's Diseases; Journal of Biological Chemistry 279:13256.

JBC280:43150; W. Zhou et al; DJ-1 Up-regulates Glutathione Synthesis during Oxidative Stress and Inhibits A53T alpha-Synuclein Toxicity; Journal of Biological Chemistry 80:43150.

JJP82:85; K. Sugaya et al; New Anti-inflammatory Treatment Strategy in Alzheimer's Disease; Japanese Journal of Pharmacology 82:85.

NATIMMU9:857; A. Halle et al; The NALP3 inflammasome is involved in the innate immune response to amyloid-beta; Nature Immunology 9:857.

NBA23:655; D. A. Butterfield et al.; Evidence that amyloid beta-peptide-induced lipid peroxidation and its sequelae in Alzheimer's disease brain contribute to neuronal death; Neurobiology of Aging 23:655.

NCHEMINT39:141; C. B. Pocernich et al; Glutathione-elevation and its protective role in acrolein-induced protein damage in synaptosomal membranes: relative to brain lipid peroxidation in neurodegenerative disease; Neurochemistry International 39:141.

NEUR0173:150; G. Leung et al; Anti-acrolein treatment improves behavioral outcome and alleviates myelin damage in Experimental Autoimmune Enchephalomyelitis mouse; Neuroscience 173:150.

NYTIMES2007:0121A; G. O'Mullan et al; Sniffing Out the Truth; The New York Times, Jan. 21, 2007.

NYTIMES2007:0121B; L. Turin; What You Can't Smell Will Kill You; The New York Times, Jan. 21, 2007.

PHYRES3:50; S. Nakagawa et al; Prevention of Liver Damage by Aged Garlic Extract and Its Components in Mice; Phytotherapy Research 3:50.

PLONE6:E16746; A. Rakovic et al; Mutations in PINK1 and Parkin impair ubiquination of mitofusins in human fibroblasts; PLoS ONE 6:E16746.

PNAS90:9649; D. E. Schemechel et al; Increased amyloid beta-peptide deposition in cerebral cortex as a consequence of apolipoprotein E genotype in late-onset Alzheimer disease; Proceedings of the National Academy of Science 90:9649.

QD3.A5#159:577; American Chemical Society; Formaldehyde; Monograph series volume #159, American Chemical Society.

QK475.A43B56; E. Block; Garlic and Other Alliums— The Lore and the Science; RSC Publishing, Cambridge, UK.

QP606.G59G59; N. Vermeulen et al, 1996; Glutathione S-Transferases: Structure, Function and Clinical Implications; Taylor & Francis Ltd., London, England.

QP606.G59G59:199; T. Ishikawa and K. Akimaru; Transport of Glutathone S-Conjugates from Cancer Cells: Function and Structure of the GS-X Pump (in QP606.G59G59).

QP801.A33S3; E. Schauensteni et al, 1977, Aldehydes in Biological Systems—Their Natural Occurrence and Biological Activities; Pion Limited, London.

QP801.A33S3:68; FIG. 3.10 (in QP510.A33S3).

RB170.H36; E. Cadenas and L. Packer, 2002; Handbook of Antioxidants; Marcel Dekker, Inc. New York, N.Y.

RB170.H36:235; W. G. Seims et al; Oxidative Breakdown of Carotenoids and Biological Effects of Their Metabolism (in RB170.H36).

RM666.G15K6313; H. P. Koch and L. D. Lawson, 1996; GARLIC The Science and Therapeutic Application of *Allium sativum* L. and Relates Species; Williams & Wilkins, Baltimore, Md.

RM666.G15K6313:42; H. P. Koch and L. D. Lawson; Table 3.3 Total Known Sulfur Compounds in Whole and Crushed Garlic Cloves (Page 42 in RM666.G15K6313).

RM666.G15K6313:93; H. P. Koch and L. D. Lawson; Table 3.17 Comparison of Commercial Garlic Products Available in 1990 for Yield of Total Known Sulfur Compounds (Page 93 in RM666.G15K6313).

RS403.H33:393; P. H. Stahl et al; Handbook of Pharmaceutical Salts—Properties, Selection, and Use; Wiley-VCH, Zurich 2011.

U.S. Pat. No. 7,678,833; D. M. Ott; Method to Increase the Bioavailability of Cysteine; U.S. Pat. No. 7,678,833.

U.S. Pat. No. 8,217,084; D. M. Ott; Medicinal Products Incorporating Bound Organosulfur Groups; U.S. Pat. No. 8,217,084.

3. Description of the Published Art 3.1 New Knowledge about the Causes of Neurological Diseases Modern methods greatly increase the amount of physiological detail which can be measured or observed, and in some cases causing revisions to long-held beliefs. This is especially true now that genetic information is available for the entire human genome.

Diseases associated with gross genetic defects have been known for decades, but only a small minority of the population inherit a genetic defect which, in and of itself, produces a disease. Most genetic diseases are now known to be associated with a combination of genetic alleles (none of which can individually cause the disease), or the combination of one or more genetic alleles with environmental factors.

Because Alzheimer's and Parkinson's diseases are both the most prevalent and the most researched of the neurodegenerative diseases, the description below will concentrate on these diseases.

3.2 Examples 3.2.1 Alzheimer's Disease 3.2.1.1 The Effect of APOE Allele Type on Alzheimer's Disease Risk The new techniques allow the influence of genetic alleles to be accurately determined, which can provide deep insights into the disease process itself. A good example is that of apolipoprotein E (APOE) which has three major human isoforms which are designated e2, e3, and e4. The e4 allele of APOE is associated with an increased risk of developing Alzheimer's disease (NBA32:655); while the e2 allele of APOE decreased the risk relative to the e3 allele (which is considered "normal" because the e3 allele is found in the majority of the population of the world).

The alleles of APOE vary at only two codons, with the e4 allele coding for an arginine at both 130Arg and 176Arg, the e3 allele coding for a cysteine at position 130Cys and an arginine at position 176Arg, and the e2 allele coding for cysteines at both positions 130Cys and 176Cys(BMCBBF2: 13). For those with two copies of the e4 allele, their likelihood for developing early onset Alzheimer's disease is over 6 times as great as for those with two copies of the e3 allele, and over 11 times as great at that for those who have one copy of the e3 allele and one copy of the e2 allele (there were no e2/e2 patients within the population surveyed) (BMCBBF2:13).

These statistics are very close (over 6 vs. almost 7) to the relative frequency of strongly reactive amyloid-beta-immunoreactive plaques found in the hippocampus of autopsied patients with late-onset sporadic Alzheimer's disease, which is observed to be almost 7 times greater for APOE4/4 patients than for APOE3/3 patients (two copies of e4 vs. two copies of e3) (PNAS90:9649).

One reason for the observed relationship between the number of cysteines in each APOE allele and the the prevalence of amyloid-beta plaques found in the autopsied brains is explained in the paper "Evidence that amyloid-beta-peptide-induced lipid peroxidation and its sequelae in Alzheimer's disease brain contribute to neuronal death" (NBA23:655). Briefly stated, in the order from observed result to ultimate cause:

a. amyloid-beta plaques contain cross-linked proteins.
b. the cross-links of the proteins are formed by two proteins conjugating with an alpha,beta-unsaturated aldehyde.
c. the first observed conjugation product of an alpha,beta-unconjugated aldehyde and a protein is a protein carbonyl (which is commonly regarded as an indication of protein oxidation), the frequency of which is almost 2 times greater for the e3 allele vs. the e2 allele, and almost 3 times greater for the e4 allele vs. the e2 allele.

d. therefore, the e2 allele has a significant antioxidant effect (the inhibition of protein carbonyl formation) that is not shared by the cysteine deficient e4 allele.

As dramatically shown by FIG. 10 (from NBA23:655), the degree of protection from carbonyl formation is directly proportional to the number of free cysteines available. The drop from e4 to e3 is equal to the drop from e3 to e2, indicating that each APOE free cysteine makes an equal contribution to the inhibition of protein carbonyl formation.

3.2.1.2 Mutations to Amyloid Precursor Protein (APP)

The first mutations discovered in familial Alzheimer's disease were missense mutations in APP which have the effect of increasing the production of amyloid-beta and its progressive accululation in the brain. This led to the "amyloid hypothesis" of Alzheimer's disease progression. However, most cases of early onset Alzheimer's disease do not have a mutation in APP.

3.2.1.3 Mutations in Presenilin-1 and Presinilin-2

Mutations in the presenilins account for the majority of familial Alzheimer's disease cases. These mutations increase the level of amyloid-beta peptide that is produced in the brain. Mice mutated to express human amyloid precursor protein and mutated human PS-1$^{P264L}$ genes develop significantly elevated lipid peroxidation (as indicated by protein-bound HNE) and protein oxidation (as indicated by protein carbonyls). By age 1 month, the levels of protein-bound HNE and protein carbonyl levels in the brain have both increased by 40% compared to controls. Furthermore, the early progression and regional distribution of amyloid-beta deposits (e.g. in the frontal cortex) match those of Alzheimer's disease (FRBM45:1420).

3.2.2 Parkinson's Disease

3.2.2.1 Gene Mutations Linked to Familial Early Onset Parkinson's Disease

Alpha-synuclein is a small protein that is expressed in many parts of the brain. Mutations in the alpha-synuclein gene (PARK1) are a very rare cause of Parkinson's disease. Although the clinical features associated with alpha-synuclein mutations are the same as those of ideopathic Parkinson's disease, including the formation of Lewy bodies and the development of cognitive impairment, the age of onset is lower and the rate of disease progression is more rapid.

Mutations to the parkin gene (PARK2) and the "PTEN-induced putative kinase 1" (PINK1) gene produce clinical symptoms similar to ideopathic Parkinson's disease, including substantial loss of dopaminergic neurons in the substantia nigra region of the brain, but there is a lack of Lewy body formation.

The physiological role of parkin is the ubiqiunation of proteins destined to be catabolized. PINK1 works with parkin to maintain mitochondrial integrity. Mitochondria exposed to oxidative stress are normally cleared from the cell via mitophagy, but mutated PARK2 or PINK1 reduce the efficiency of this process. Because mitophagy is the only way that mitochondria are recycled, in its absence defective mitochindria accumulate in the cell (PLONE6:E16746).

Mutations to the DJ-1 gene at the PARK7 locus can also cause familial early onset Parkinson's disease. Wild type DJ-1 can prevent dopaminergic cell death by two different protection mechanisms (JBC280:43150). First, during oxidative stress, expression of DJ-1 increases glutathione synthesis by increasing both the transcription and enzymatic activity of the rate-limiting enzyme, glutamine-cysteine ligase (GCL). Secondly, in response to alpha-synuclein overexpression, wild type DJ-1 activated the molecular chaperon protein Hsp70, which blocks alpha-synuclein aggregation and toxicity. The loss of either of these functions due to DJ-1 mutations would increase vulnerability to the development of Parkinson's disease.

3.3 Evidence for Inflammatory Positive Feedback in Alzheimer's and Parkinson's Diseases

3.3.1 Alzheimer's Disease

The gene mutations described above that are associated with Alzheimer's disease and Parkinson's disease all relate to protein aggregation, defective clearance of protein aggregates, and the oxidative stress which leads to protein aggregation. Furthermore, the protein aggregates typically induce an immune response that produces oxidative stress, and that oxidative stress causes lipid peroxidation. Lipid peroxidation products in turn produce cross links between proteins, which then cause inflammation and more oxidative stress.

Activated astrocytes and microglia play a major role in the inflammation observed in Alzheimer's disease as well as many other neurological diseases. In Alzheimer's disease, amyloid plaques are surrounded by astrocytes and activated microglia which release inflammatory cytokines such as Interleukin-1 IL-1), Interleukin-6 (IL-6), and tumor necrosis factor (TNF) alpha (JALHZD4:193). These in turn activate cyclooxygenase-2 (COX-2), Nuclear Factor kappa B (NFkB), iNOS expression (inducible nitric oxide synthase) and the production of reactive oxygen species (ROS) such as hydrogen peroxide and peryoxinitrite (JBC275:7918).

The activation of NFkB appears to also directly increase the production of Amyloid Precursor Protein (APP), because the APP gene has a binding site for the NFkB transcription factor in its 5'-regulatory region (JJP82:85).

Conversion from diffuse non-neurite plaques to the neuritic plaques is diagnostic of Alzheimer's disease. The fibrillar state of amyloid beta is a requirement for IL-1 beta release (NATIMMU9:857). Furthermore, amyloid beta phagocytosis by microglia is necessary for that pathway. Once amyloid beta is phagocytosed by microglial cells, lysosomes that contain amyloid beta adopt a swollen morphology, structural damage, and loss of membrane integrity. This is because microglia are incapable of efficiently degrading fribular amyloid beta, even over a period of weeks after its internalization. The uncontrolled release of lysosomal components into the cytoplasm is proinflammatory. For example, the cathepsin B released from the lysosomes induces microglial IL-1 beta release (NATIMMU9:857).

It is interesting to note that cross-linked protein aggregates are also resistant to the digestive system. Formaldehyde (an aldehyde that forms protein cross-links) is prohibited by law from use as a food preservative because formaldehyde-modified proteins are not digestible (QD3.A5#159:577). Similarly, collagen that is treated with formaldehyde is inert towards proteolytic enzymes (QP801.A33S3:13). Furthermore, aldehydes, especially alpha,beta-desaturated aldehydes, inhibit the enzymes of digestion (QP801.A33S3:15)

3.3.2 Parkinson's Disease

Neuroinflammation and alpha-synuclein aggregation potentiate each other, driving chronic progression of neurodegeneration in a mouse model of Parkinson's disease. A new mouse model of Parkinson's disease uses a single lipopolysaccharide infusion to trigger a Parkinsonian disease which more closely mimics the human disease than other available animal models (EHP119:807):

"a) chronic, progressive, and relatively specific degeneration of dopaminergic neurons and fibers in the nigostriatal pathway;
b) Lewy body-like neuronal inclusions containing aggregated alpha-synuclein;
c) persistent neuroinflammation, a common feature shared by all neurodegenerative diseases including PD; and
d) a chronic progressive disease course that is absent in most available PD models."

This demonstrates the "neuroinflammation to protein aggregation to more inflammation loop" is in action, in the best available animal model for Parkinson's disease.

3.3.3 Oxidative Stress, Lipid Peroxidation, and Aldehydes in the Inflammatory Positive Feedback Loop Although a wide variety of aldehydes (including simple aldehydes such as formaldehyde) can form protein cross-links, the alpha,beta-unsaturated aldehydes contain one (or more) carbonyls and one (or more) carbon-to-carbon double bonds which can readily react with the protein side groups of cysteine, lysine or histidine. Among the aldehydes that are produced in vivo, acrolein is the most reactive (pure acrolein is self-explosive!) but HNE (4-hydroxy-2-nonenal) seems to be the most researched.

FIG. 2 illustrates that inflammation 21 induces the production ROS (such as nitric oxide, peroxynitrite, and hydrogen peroxide) which cause lipid peroxidation 22 in biological membranes. The spontaneous degradation products of lipid peroxides include a variety of aldehydes, including the alpha,beta-unsaturated aldehydes HNE and acrolein.

These aldehydes readily form reversible protein adducts 23 with the cysteine, lysine or histidine amino acids of proteins. Although the adducted proteins may lose their function, the adduction is reversible, perhaps allowing the protein to be repaired by the removal of the aldehyde (which can occur spontaneously). But when exposed to reactive oxygen species (ROS), further reactions can occur, including the formation of irreversible protein-aldehyde adducts 24 (CRT11:247). The irreversible adducts can permanently prevent the protein from performing its functions, impairing the performance of the cell until the damaged protein is replaced.

The irreversible adducts, when further exposed to ROS, can form irreversible cross-links between proteins. The resulting protein aggregation 25 is proinflammatory and can activate microglia, resulting in inflammation 21. This feedback loop can be self-sustaining, leading to the progressive degeneration that is seen in Alzheimer's and various other neurodegenerative diseases.

4.0 Summary of the Invention

A primary goal of the invention is to break the feedback loop of inflammation leading to damaged molecules which can then lead to further inflammation and tissue damage. By decreasing the formation of the protein-aldehyde adducts that can produce protein aggregates, unnecessary inflammation is prevented. Lipophilic mercaptan molecules can detoxify aldehydes by rapidly conjugating with them, thereby protecting proteins and other biomolecules such as DNA from damage. Lipophilic mercaptan molecules can also repair damaged protein residues by participating in exchange reactions that remove the aldehyde adducts from the proteins.

This process is illustrated in FIG. 3. Firstly, it is worth pointing out that much of the action shown occurs within the lipid membranes of cells. Inflammation 31 produces reactive oxygen species (ROS) which encounter lipophilic mercaptan molecules within the lipid membranes. The lipophilic mercaptans can detoxify almost every type of ROS (perhaps every type), producing less toxic molecules indicated here as "scavenged ROS" 36. This scavenging prevents the ROS from causing lipid peroxidation 32. (Note that the two short cross-lines on the arrow from 31 to 32 indicate inhibition or diversion to another path.)

Should lipid peroxidation occur (for any reason), the peroxide degradation products will include aldehydes. These aldehydes will encounter lipophilic mercaptans close to their source of origin (i.e. within the lipid membrane itself), reacting with the lipophilic mercaptans to form less toxic scavenged aldehydes 37. The scavenging of the aldehydes prevents the formation of reversible protein-aldehyde adducts 33.

Should reversible protein aldehyde adducts form (for any reason), the lipophilic mercaptans can repair the protein by trans-adduction, thereby repairing the protein 38. Alternatively, lipophilic mercaptans can prevent the formation of an irreversible protein-aldehyde adducts by scavenging ROS molecules 39 before they can convert a protein adduct from a reversible to an irreversible one.

Thus, lipophilic mercaptans can break the feedback loop at several steps within the loop. Note that among antioxidants, only mercaptans (or other thiols) can detoxify aldehydes or repair adducted proteins by trans-adductation. And only mercaptans that are located within the lipid membranes of the cell can detoxify aldehydes at their source and protect (or repair) proteins that are located in membranes.

The lipophilic mercaptans are preferably administered in the novel form of a mixed disulfide with N-acetylcysteine, which releases the lipophilic mercaptans in the body via thiol-disulfide exchange reactions. These molecules could be developed and deployed as drugs. But because the mixed disulfide has much lower objectionable smell and taste than the lipophilic mercaptan itself, in some cases it can be suitable for administration as a dietary supplement or as a nutraceutical food.

The specific mixed disulfides include S-allyl-N-acetylcysteine and S-propyl-N-acetylcysteine which incorporate organosulfur groups that are found in natural crushed garlic and the steam distilled products of crushed garlic and onions. These form allyl mercaptan and propyl mercaptan in the body, which are lipophilic compounds that are already FDA approved for use in food.

Other aspects, advantages, and novel features of the invention are described below or will be readily apparent to those skilled in the art from the following specifications and drawings of illustrative embodiments.

5. Brief Description of the Drawings

6 Detailed Description of Illustrative Embodiments

6.1 Detoxification Pathways

6.1.1 In Biological Systems, Aldehydes Preferentially Attack Sulfhydryl Groups This is a good place to start the detailed description, because whenever free SH groups are available, they are first in line for being attacked by aldehydes. For example, although HNE will readily react with the amino groups of proteins (see FIG. 5A) in the absence of available SH groups, experiments show that for concentrations of HNE from $10^{-5}$ to $10^{-3}$ M, and for a duration of several hours, the HNE will will attack "practically only sulfhydryl groups" (QP801.A33S3:4). Compared to the reaction with amino groups, the reaction with SH groups "takes place much faster, in fact by several orders of magnitude" (QP801.A33S3:5). At neutral pH and room temperature, the reaction rate with SH groups is approximately one mole per second (QP801.A33S3:27). Note that because the reaction with an amino group is spontaneously reversible, any such reactions that occur will soon be reversed, and the aldehyde is likely to next attack an SH group instead of the previous amino group.

Figure 5A:
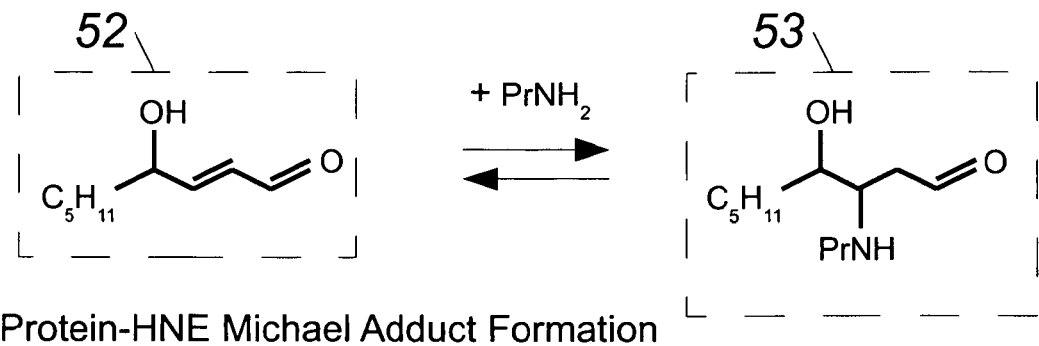
FIG. 5A through FIG. 5B show the reversible Michael adduct formation between HNE and a protein.

Although the alpha,beta-unsaturated aldehydes have two sites that are reactive with cysteine, the Michael addition reaction at the C=C site is preferred (QP801.A33S3:5), with the cysteine eliminating the C=C double bond of the aldehyde (similar to the reaction of FIG. 5A, with PrSH replacing $PrNH_2$ in the reaction). (The other reaction is a Michael addition that has the cysteine eliminating the C=O double bond of the aldehyde.) Again, because any reaction at the C=O site is spontaneously reversible, the aldehyde is likely to next react at the more favorable C=C site.

6.1.2 Small Molecular Weight Thiols Effectively Protect Protein Thiols from Aldehydes In general, aldehydes are more reactive with the SH groups of small molecular thiols that with any other type of molecule found in biological systems. This is true even in comparison with the SH groups of proteins.

Figure 4:
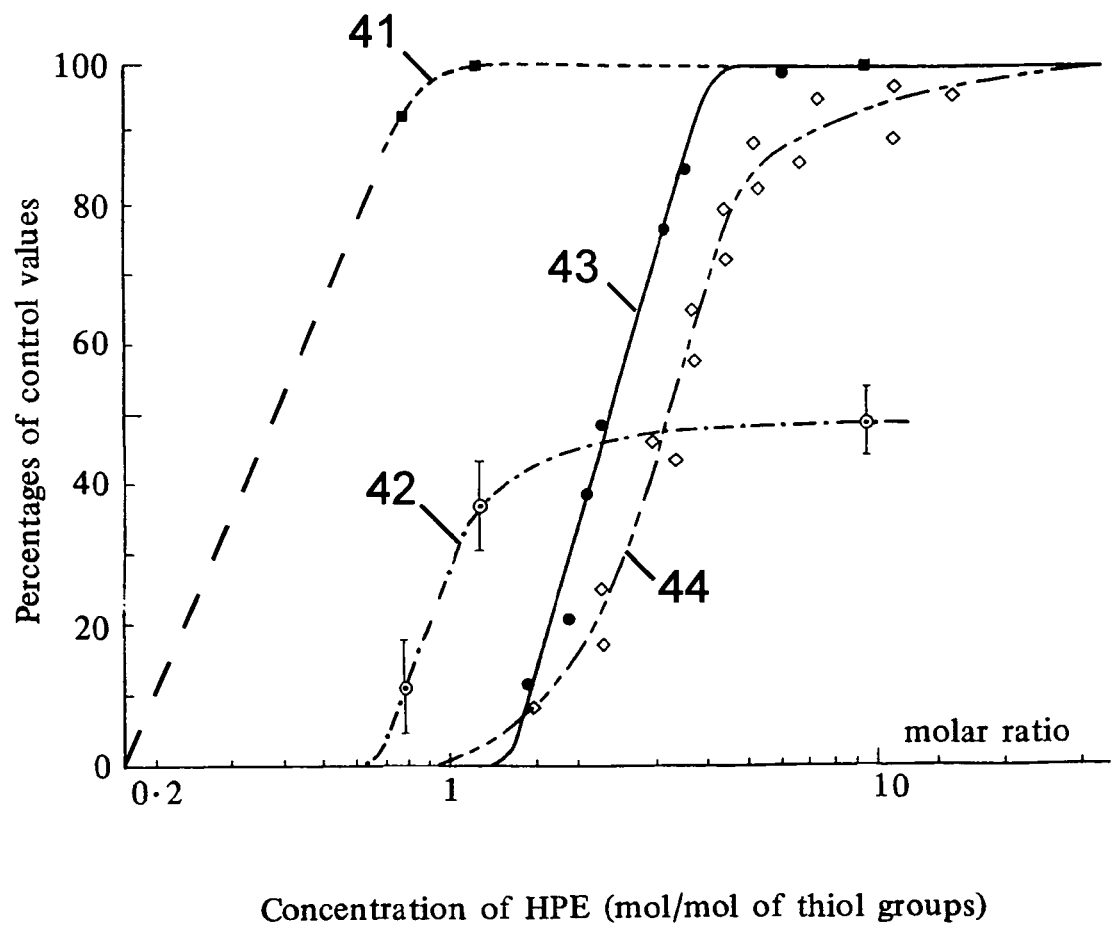
FIG. 4 (derived from QP801.A33S3) shows HNE induced depletion of thiol groups.

FIG. 4 shows how amazingly effectively small molecular thiols protect the SH groups of proteins within actual Ehrlich ascites tumor cells (QP801.A33S3:68). The aldehyde being used is similar in structure and reactivity to HNE 15. The plotted lines show the percentage decreases of:

Low molecular weight thiols (e.g. Glutathione) 41

Soluble (e.g. cytosolic) protein sulfhydryls 42

Inhibition of glycolysis (e.g. enzyme activity) 43

Inhibition of respiration (e.g. $O_2$ consumption) 44

For intracellular concentrations of HPE up to 0.6 mM, the low molecular weight thiols become depleted, but there is no effect on protein sulfhydryls or enzyme activities. Only after the low molecular weight thiols are more than 80% depleted do the protein sulfhydryls even start to become affected. Only after 100% of the low molecular weight thiols are depleted and 30% of the protein sulfhydryls have been depleted (blocked) does enzyme activity become affected.

The authors' primary explanation for this is that:

"The preferred reaction of the NPSH [[low molecular weight thiols]] may be explained by their greater accessibility to HPE [[the aldehyde]], whereas the $PSH_s$ [[soluble protein thiols]] are partly more difficult of access or not accessible at all (masked sulfhydryl groups), that is to say they remain less reactive, because of the structure of the proteins and the cell compartments."

But I think that the real reason is that there is a continuous transfer of aldehydes from whatever protein adducts that do form to the low molecular weight thiols that are floating around within the cytosol of the cell. This "trans-adduction" process that I propose is analogous to the "transglycation" process that has been shown to transfer the glucose moiety of protein-glucose conjugates to free cysteine molecules, thereby repairing glycated proteins (U.S. Pat. No. 7,678, 833).

Note that when the low molecular weight thiols are not depleted, the protein SH groups are essentially fully protected from modification by the aldehyde. But when the small molecular weight thiols become depleted, the protein SH groups are essentially completely unprotected.

6.1.3 Other Types of Antioxidants do not Protect Proteins from Aldehydes, and in Fact can Make Things Worse Although "SH" based antioxidants such as cysteine and glutathione are protective, other commonly used antioxidants such as Vitamin A, Vitamin C, and Vitamin E provide no protection, and can actually make things worse.

Although vitamin C and glutathione in many ways work together and vitamin C can partially substitute for glutathione as an antioxidant, excessive vitamin C consumption has been shown to significantly decrease the glutathione content of cells. This effect has been utilized in a clinical trial where the goal was to increase the cytotoxicity of the chemotherapeutic drug arsenic trioxide (which is normally detoxified by glutathione within cells) against the cancer multiple myeloma (CCR8:3658). A daily dosage of 1000 mg of vitamin C caused significant glutathione depletion, resulting in a mean percentage decrease of 60% among the patients.

Vitamin A and other carotenoids can also cause depletion of glutathione and other thiols. The main antioxidant property of the carotenoids is the quenching of singlet oxygen, with each carteniod molecule able to do this approximately 1000 times before it breaks down and forms a very reactive aldehyde molecule. These break down products form adducts with SH groups that are not reversible. Carotenoid breakdown products are otherwise long lived and can travel far before they encounter (for example) an SH sensitive enzyme, producing a cumulative inhibition of SH enzymes in the body. Carotenoid levels, especially beta-carotene in blood and various tissues are dependent on the carotenoid content of food and may exceed the levels that were used in these enzyme inhibition studies (RB170.H36:235).

Note that this apparently little-known toxicity of carotenoids may explain the poor results from the "beta-Carotene and Retinol Efficacy Trial", which showed that carotenoid supplementation significantly increases cancer risk and overall mortality (CBEP12:350).

6.1.4 Reactions between Aldehydes and Thiols Also Occur in Hydrophobic Environments The aldehydes that are formed as lipid peroxide degradation products are sufficiently water soluble to enter the cytosol of the cell and diffuse to diverse targets (including nuclear DNA). This has led most researchers to conduct their in vitro experiments in aqueous systems instead of non-polar oils or solvents. They have firmly established that aldehydes rapidly react with thiols in water, but leave the question of whether such reactions also can occur in nonpolar, aprotic environments such as within lipid-based membranes.

However there is experimental evidence that aldehydes can participate in Michael addition reactions with both cysteine and lysine residues of proteins in hydrophobic environments within cells and also in a model system using an nonpolar aprotic solvent (hexane). The enzyme fructose-1,6-bisphosphatse is inactivated by the aldehyde o-phthalaldehyde which creates an irreversible intra-protein crosslink between a cysteine residue and a nearby lysine residue. Because the "molar transition energy" can be used to determine the degree of polarity in the microenvironment of the cysteine and lysine residues participating in the reaction, the molar transition energy of the adduct (121 kJ/mol) was well matched to that which was obtained from an analogous model reaction performed in hexame (121 kJ/mol), indicating that the environment within the protein where the reaction occurs must be a hydrophobic environment (BBRC150:1088).

Note: Amyloid beta, alpha-syneuclein and APOE all are proteins which preferentially locate within membranes.

6.1.5 Aldehyde Adduct Formation with Protein Lysine Residues

In the absence of low molecular weight thiols, adducts can readily form between aldehydes and protein lysine residues ($PrNH_2$) by a Michael addition reaction, as shown in FIG. 5A.

The aldehyde HNE (52 of FIG. 5A) will react with the lysine amino group ($NH_2$) of a protein (Pr) with the nitrogen of the amino group bonding to one carbon atom of the aldehyde's C=C double bond and one of the two H atoms of the amino group bonding with the other carbon atom of the double bond. As shown in 53 of FIG. 5A, the adduct is attached to the Nitrogen atom of the protein by a single bond, and the nitrogen atom still retains one of the hydrogen atoms.

6.1.6 Most Protein-Aldehyde Adducts are Protein Carbonyls

As shown in 53 of FIG. 5A the protein-aldehyde adduct has added to the protein an exposed oxygen that is double bonded to a carbon (a carbonyl group, PrC=O). The most widely used marker for oxidative damage to proteins is the introduction of carbonyl groups.

Elevation in the total level of protein carbonyls has been documented in both Alzheimer's and Parkinson's diseases (JBC279:13256). In particular, the protein "Ubiquitin Carboxyl-terminal Hydrolase L1" which is associated with mutations of the UCH-L1 gene in a rare familial form of Parkinson's disease, is also seen to be significantly carbonylated in the idiopathic versions of both diseases. These oxidative modifications may cause irreversible alteration to the catalytic activity (e.g. the clearance of damaged proteins via ubiquination and subsequent proteolysis) and have a deleterious effect on neuronal function and survival (JBC279:13256).

6.1.7 Protein Repair by Low Molecular Weight Thiols (e.g. Mercaptans)

Figure 5B:
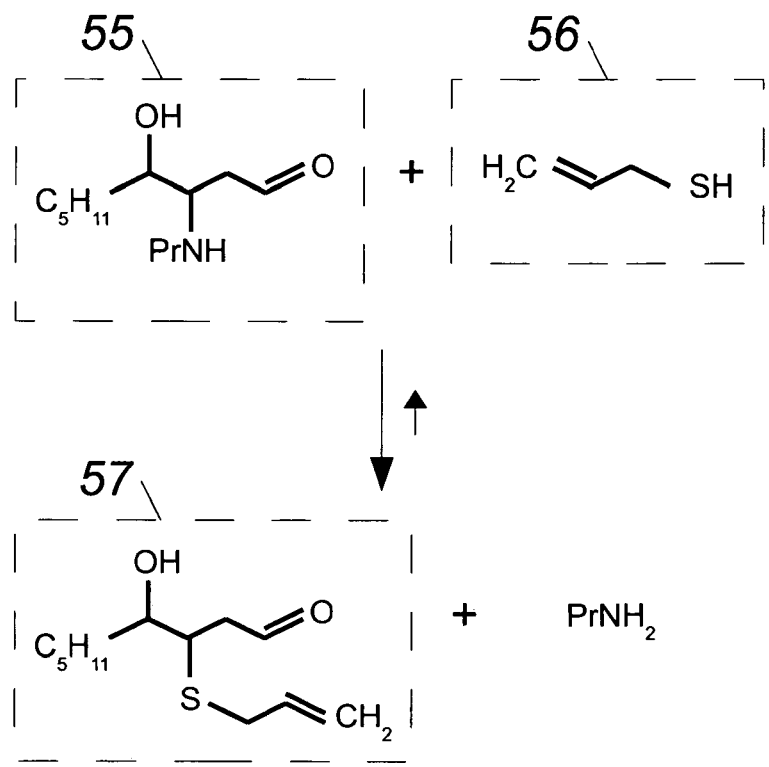

Mercaptans are low molecular weight thiols that are well suited for repairing adducted proteins via trans-adduction. FIG. 5B shows that allyl mercaptan 56 can exchange with the protein in the protein-HNE adduct 55 to form an allyl mercaptan-HNE adduct 57 instead (with the protein emerging fully repaired as $PrNH_2$). Because the aldehyde has much greater affinity for the SH group of the mercaptan than it does for the NH group of the protein, the reaction is rapid and is irreversible in practice.

The reaction that is being called "trans-adduction" here is similar to the well known nucleophilic substitution reaction (where the more "electron rich" nucleophile attacks a molecule that contains a less electron rich nucleophile (which when it leaves is called the "leaving group"). In this case the attack comes from both the "S" and the "H" of the mercaptan which both attach to the aldehyde, and the leaving group is the entire protein.

6.1.8 Further Evidence that Low Molecular Weight Thiols (e.g. Mercaptans) can Protect Proteins in Membranes from Aldehydes Glutathione Ethyl Ester (GEE) is a glutathione analog that is formed by adding an ethyl group to the C-terminus carboxyl group of glutathione, thereby converting glutathione into an electrically neutral molecule. This allows GEE to enter cells by diffusion through the cell membrane (ABB239:538).

Figure 7:
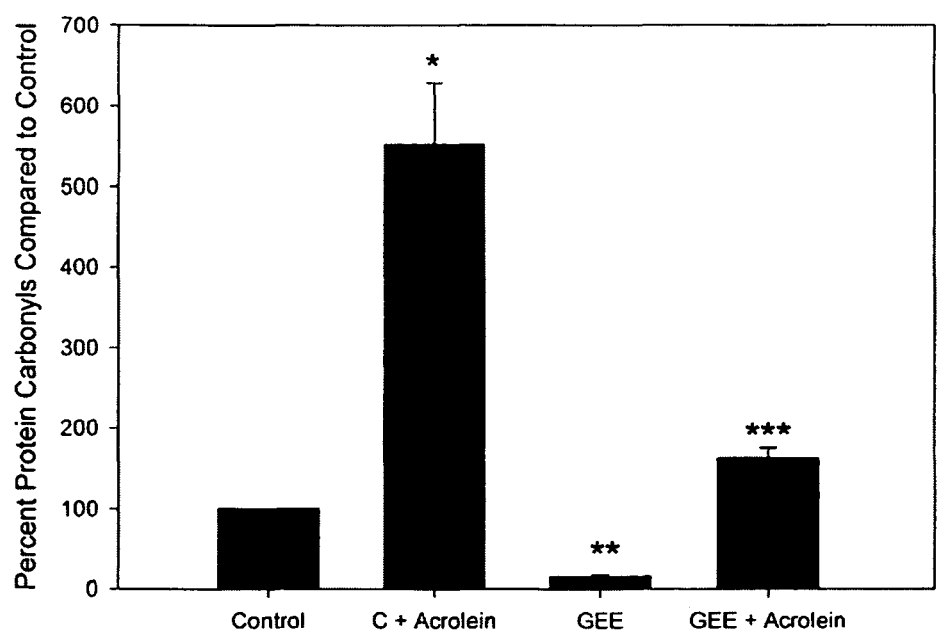
FIG. 7 (from NCHEMINT39:141) shows that Glutathione-Ethel-Ester decreases protein carbonyls compared to controls.

Pretreatment of synaptosomal membranes with GEE significantly reduces the amount of protein carbonyls that are observed after acrolein treatment (FIG. 7, from NCHEMINT39:141). The "C+Acrolein" bar increases to 552% of "Control", while the "GEE+Acrolein" bar only increases to 163% of "Control". These results are consistent with the results of others, which consistently show a protective effect from the elevation of glutathione prior to exposure to aldehydes.

But the really interesting result is that the "GEE" column (positive control) has an 85% lower concentration of carbonyls in the synaptosomal membrane than the "Control" column.

The authors state that:
"This decrease in protein carbonyls suggests. that GEE protected synaptosomes from auto-oxidation from exposure to oxygen in the air."

If so, this shows that membrane was protected from carbonyl formation by the GEE in the membrane.

But perhaps that is not the only thing going on. These results could also indicate that the GEE can remove previously formed carbonyls from the proteins in the membrane (trans-adduction of protein-aldehyde adducts). The dramatic reduction in carbonyls seems to exceed the amount that would normally be expected from only 3 hours of oxygen exposure (the duration of GEE pretreatment in the experiments).

6.1.9 Irreversible Adduct Formation has a Low Probability but a High Toxicity The reactions that produce reversible protein-aldehyde adducts include Michael additions to protein cysteine, lysine, and histidine and also Shiff base additions to lysine. These addition reactions are all spontaneously reversible at a low rate. They are also rapidly reversed by trans-adduction reactions with mercaptans.

Although this disclosure has emphasized (and will continue to emphasize) the formation of irreversible protein cross-links, their formation is relatively rare compared to the rate of reversible adduct formation (and reversal) within any biological system that includes a significant level of mercaptans. This is not to say that the short-term formation of adducts is without effect. For example, many (probably most) enzymes include one or more cysteines whose blockage by aldehyde adduct formation will impair the function of the enzyme. But because this blockage is reversible, the effect is temporary and is unlikely to kill the cell.

Of the irreversible cross-links that are seen in detergent insoluble protein aggregates, lysine is almost always involved. Furthermore, the fluorescent "signature" of a wide variety of these aggregates show evidence of the formation of a pyrrole ring (a 5-sided ring of 4 carbons and one nitrogen with attached side groups). In particular, the pyrrole-based cross link shown in FIG. 6B 68 is representative of the irreversible cross-links with this fluorescent signature CRT11:247).

The formation of the pyrrole-based cross link requires a relatively long and specific sequence of steps (presented in detail in CRT11:247, and summarized in FIG. 6B and in the disclosure below). But it is not likely that all of these steps are specifically "favored" throughout the process. It is just that the various other possibilities don't tend to result in the formation of a permanent, irreversible cross-link.

Figure 6A:
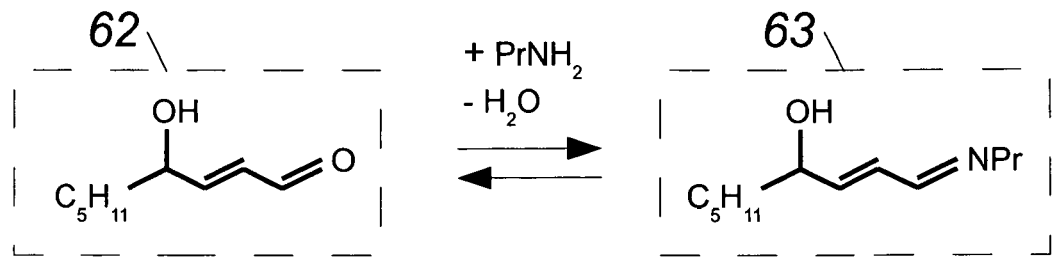
FIG. 6A through FIG. 6B show HNE induced irreversible cross-link formation between two proteins.
Figure 6B:
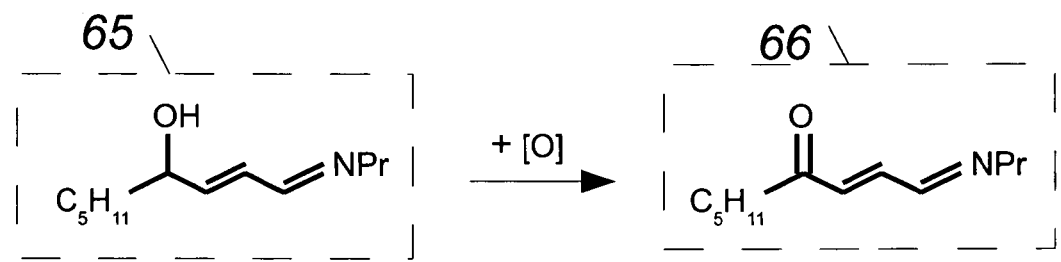
Figure 6B:
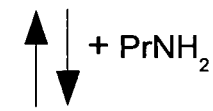
Figure 6B:
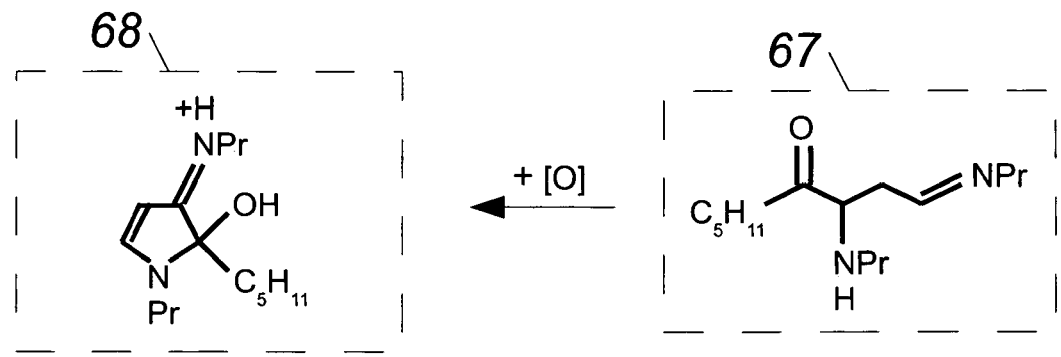

For example, the very first step is the formation of a Schiff base between an aldehyde 62 and a lysine of a protein "PrNH$_2$" to form a reversible protein-aldehyde adduct 63 (as shown in FIG. 6A). (This adduct is the starting point for the irreversible adduct formation process shown in FIG. 6B.) Note that this Schiff base cross-link remains unchanged until the final step of the process (ring formation 68). During this entire time, this cross-link could be reversed by a trans-adduction reaction with a mercaptan. But any reaction path that includes this reversal would not produce a permanent end product, and would not cause an accumulation of similar molecular structures that could be observed after the fact.

To reiterate, the molecule shown as 65 could easily be reversed, as could the molecule shown as 66, as could the molecule shown as 67, if mercaptans are present in the system.

Although reversals occur all the time, with a sufficiently long time a significant level of cross-linked proteins can eventually accumulate, and these can become easily observable (e.g. as age spots in the skin of old people).

However, as illustrated by FIG. 4, time isn't necessary for the accumulation of early protein-aldehyde adducts (e.g. protein carbonyls) if the mercaptans in the system become depleted.

If the "system" is located in a lipid membrane, it is lipophilic mercaptans located in the membrane that are needed for the efficient reversal of the initially formed protein-aldehyde adducts (before they can become irreversible).

6.1.10 Cysteine Deficiency

In U.S. Pat. No. 7,678,833 I spend several pages making the case that there is probably a significant cysteine deficiency associated with current dietary practices, which I won't repeat here. But one point is directly relevant.

In 2001, it was reported that the current recommendation for daily dietary sulfur amino acid consumption were low by almost a factor of two (13 mg/kg instead of 25 mg/kg) due to an arithmetic error when the requirements were determined experimentally in 1955 (AJCN74:756). Therefore, a 70 kg person should actually be consuming 1750 mg of sulfur amino acids per day (of which approximately ½ will be cysteine and ½ will be methionine). Another problem with the way that the dietary sulfur amino acid requirements were determined is that the experiments were based on "nitrogen balance" which only measures the amount of the amino acid that is needed for protein formation (weight maintenance) and does not take into account other biological requirements for cysteine (such as the synthesis of glutathione, taurine, and sulfate).

Therefore, even if someone is consuming the amount of cysteine that is currently officially recommended, this may actually be less than half of their actual dietary needs.

6.2 Pharmacological Intervention Options

6.2.1 Mercaptans Themselves are Poorly Suited for Direct Administration

For one thing, they are extremely smelly. In U.S. Pat. No. 7,678,833 compositions are disclosed that utilize a dietary protein (whey protein) with allyl mercaptan disulfide bonded to the cysteine residues of the protein as a lower taste and smell way of administering allyl mercaptan. The allyl mercaptan is only released from the protein when the protein is digested. But because the amount of cysteine in the protein is only 2% of the protein by weight, the amount of allyl mercaptan that can be contained in the capsule is limited by the bulk of the protein. What is needed in order to improve upon this is something closer to a 1:1 ratio between the allyl mercaptan and the non-volatile molecule that it is disulfide bonded to.

N-acetylcysteine is my current molecule of choice for this purpose. It is a nontoxic prodrug for cysteine which has been used at high dosages for the treatment of acetaminophen poisoning (BMCCC6:155), and it is used as a dietary supplement. (Cysteine itself is considered toxic when used in high doses.)

6.2.2 Synthesis of S-allylmercapto-N-acetylcysteine (SAMNAC)

Thiosulfinates react rapidly with mercaptans to form mixed disulfides (U.S. Pat. No. 8,217,084). The thiosulfinate "allicin" can react with a molecule of N-actylcysteine to form a molecule of SAMNAC plus a sulfenic acid that contains an allylmercapto group. This sulfenic acid molecule reacts rapidly with a second molecule of N-acetylcysteine to yield a second molecule of SAMNAC plus a molecule of water. These reactions between thiosulfinates and mercaptans are well known and are very rapid, and therefore were expected by the applicant to produce SAM-NAC molecules with a high yield.

Figure 9A:
FIG. 9A through FIG. 9D show various molecules that metabolize to form lipophilic mercaptans.

Synthesis of SAMNAC was performed for the applicant as work for hire by Larry D. Lawson, Ph.D, Research Director of Silliker Inc. Utah Laboratory, using the following procedure:
1. Starting with 1.68 mg/ml of allicin in water, measure out 10.1 mL of allicin solution=16.9 mg=0.104 mmol allicin (this is 40% excess compared to 0.15 mmol N-acetylcysteine, as one molecule of allicin reacts with 2 molecules of N-acetylcysteine to form 2 molecules of SAMNAC).
2. To a 50-mL tube, add 24.5 mg N-acetylcysteine (0.15 mmol. M.W. 163).
3. Add the 10.1 mL allicin solution to the 24.5 mg of N-acetylcysteine.
4. Shake by hand until dissolved (20-40 sec).
5. Using 2N NaOH, adjust the pH from about 2.5 to about 4.1 (takes about 0.065 mL). The reaction will not proceed at pH 2.5 but is very fast at pH 4.1
6. Rotate for 30 min (reaction probably complete in the first 2-5 min).
7. Remove the excess allicin:
   to all or part of the reaction material in step 6, add 2 volumes of DCM
   shake by hand for 30 sec
   transfer the upper layer (SAMNAC solution) to another tube
   Note: at the end of step 6, all of the N-acetylcysteine will have been used up, leaving only SAMNAC, excess allicin, some ajoene (allicin impurity), and the Na (from the NaOH, don't count the OH, as it is converted to water). Extraction with dichloromethane (DCM) removes >99% of the allicin and ajone and none of the SAMNAC, leaving only the SAMNAC, the added Na, and a trace of DCM.
8. The final amount & concentration of SAMNAC (M.W. 193) 10 mL of 15 millimolar (10 mg SAMNAC+3.0 mg added Na).
Note: The SAMNAC in solution is in the form of an anion (from the ionized carboxyl group). When the water is removed (by partial vacuum at 35 degrees C.), an oily yellow liquid id formed (which probably also contains the salt (FIG. 9A) between the SAMNAC$^-$ and the Na$^+$ that was used to set the pH of the solution).

6.2.2.1 The Hydrogen NMR Spectrum Indicates that the SAMNAC is Authentic SAMNAC Dr. Jeff Conroy of Authentix Corporation confirmed that the NRM spectrum obtained by proton NMR from the dehydrated SAMNAC is consistent with the synthesized compound being authentic SAMNAC. The NMR spectrum is:

$^1$H H NMR (CD$_3$OD, ppm): 1.99 (s, 3H), 2.99 (m, 1H), 3.31 (m, 1H), 3.36 (d, 2H), 4.44 (m, 1H), 5.091-5.21 (m, 2H), 5.79-5.93 (m, 1H).

6.2.2.2 Confirmation that SAMNAC Contains an Allyl Mercapto Group

Analysis of SAMNAC to confirm that the compound contains an allyl mercapto group was performed as work for hire by Dr. Lawson. Starting with some of the SAMNAC produced above, treatment with the reducing agent tris(2-carboxyethyl)phosphate (TCEP) produces allyl mercaptan, as verified by HPLC.

6.2.2.3 Confirmation that SAMNAC Contains an N-Acetylcysteinyl Group

Analysis of SAMNAC to confirm that the compound contains an N-acetylcysteinyl group was performed as work for hire by Dr. Lawson. Starting with some of the SAMNAC produced above, treatment with the reducing agent tris(2-carboxyethyl)phosphate (TCEP) produces N-acetylcysteine, as verified by HPLC.

6.2.3 Examples of Compositions

6.2.3.1 A "Garlic" Dietary Supplement Capsule

A dietary supplement capsule containing SAMNAC was produced by the following method:
1. Start with 5 bulbs of fresh garlic (330 g). This should produce approximately 1300 mg of allicin when pulverized, because the allicin yield from crushed garlic is approximately 4 mg/g (RM666.G15K6313:42).
2. Grate the garlic with a food processor (I used a KitchenAid food processor).
3. Transfer the "mash" to a blender (I used an Osterizer), add 200 mL of water, and blend for 10 minutes to completely pulverize the garlic.
4. Add 15 mL of N-acetylcysteine powder (11.5 g) and blend for a few seconds to mix.
5. Add sufficient potassium bicarbonate to raise the pH to approximately 4 (3.75 mL raised the pH to 4.3) and blend for a few seconds to mix.
6. Filter the fluid from the mixture by squeezing the mixture through a fine cloth. Above a cup, spoon some of the mixture onto the cloth, raise the sides of the cloth to surround the mixture, and twist the cloth to squeeze the mixture, allowing the fluid to pass through the cloth into the cup. Approximately 350 mL of liquid is obtained. The (now dry) pulverized garlic remains weigh approximately 107 g.
7. Let the fluid stand for a day at room temperature.
8. Use a food dehydrator (trays with hot air blown across them—normally used for drying fruit, vegetables, or beef jerky) to dry the fluid (I used an Excalibur). I used multiple 18-well silicone nonstick miniature donut baking molds (by Freshware) to hold the fluid, with ½ teaspoon of fluid in each well (approximately 140 wells total). Drying time is approximately 24 hours at 95 degrees F., followed by 24 hours at 155 degrees F.
9. Remove the "crystalized" product from the wells of the molds (approximately 83 g total).
10. Grind the crystalized product using a hand cheese grater (I used a Zyliss) to make a powder.
11. Fill size 00 capsules with the powder (I used the Cap-M-Quik manual capsule filler). Makes 115 capsules, each with an estimated 35 mg of SAMNAC (11 mg of allyl mercapto groups) and an estimated 75 mg of "excess" N-acetylcysteine.

I have taken these capsules at 6 per day for a month with no noticeable side effects.

6.2.3.2 An "Onion" Dietary Supplement Capsule

Just as crushing garlic produces the thiosulfinate allicin (diallyl thiosulfinate), crushing onions produces dipropenyl thiosulfinate (QK475.A43B56:150), although yellow onions only have approximately 10% of the thiosulfinate yield from garlic (approximately 0.4 mg/g). Dipropenyl thiosulfinate contains propenyl mercapto groups (analogous to the allyl mercapto groups of allicin) and has the same reaction properties. Therefore, the reaction product S-propenyl-N-acetylcysteine (analogous to S-allyl-N-acetyloysteine, SAMNAC) rapidly can be formed from the mixture of dipropenyl thiosulfinate with N-acetylcysteine at a pH of approximately 4.

A dietary supplement capsule containing S-propenyl-N-acetylcysteine was produced by the following method:
1. Start with two large fresh yellow onions (637 g, which should produce approximately 250 mg of dipropenyl thiosulfinate when pulverized).
2. Grate the onion with a food processor (I used a KitchenAid food processor).
3. Transfer the "mash" to a blender (I used an Osterizer), add 200 mL of water, and blend for 10 minutes to completely pulverize the onion.
4. Add 15 mL of N-acetylcysteine powder (11.5 g) and blend for a few seconds to mix.
5. Add sufficient potassium bicarbonate to raise the pH to approximately 4 (3.75 mL raised the pH to 4.5) and blend for a few seconds to mix.
6. Filter the fluid from the mixture by squeezing the mixture through a fine cloth. Above a cup, spoon some of the mixture onto the cloth, raise the sides of the cloth to surround the mixture, and twist the cloth to squeeze the mixture, allowing the fluid to pass through the cloth into the cup. Approximately 600 mL of liquid is obtained. The (now dry) pulverized onion remains weigh approximately 180 g.
7. Let the fluid stand for a day at room temperature.
8. Use a food dehydrator (trays with hot air blown across them—normally used for drying fruit, vegetables, or beef jerky) to dry the fluid (I used an Excalibur). I used multiple 18-well silicone nonstick miniature donut baking molds (by Freshware) to hold the fluid, with one teaspoon of fluid in each well (approximately 120 wells total). Drying time is approximately 24 hours at 95 degrees F., followed by 24 hours at 155 degrees F.
9. Remove the "crystalized" product from the wells of the molds (approximately 47 g total).
10. Grind the crystalized product using a hand cheese grater (I used a Zyliss) to make a powder.
11. Fill size 0 capsules with the powder (I used the Cap-M-Quik manual capsule filler). Makes 90 capsules, each with an estimated 8.5 mg of S-propenyl-mercapto-N-acetylcysteine (2.7 mg of propenyl mercapto groups) and an estimated 120 mg of "excess" N-acetylcysteine.

I have taken these capsules at 6 per day for a week with no noticeable side effects.

6.2.3.3 A Nutraceutical Food (Garlicky Potatoes with Bacon)

Garlicky potatoes with bacon (a nutraceutical food) was prepared in two stages. First a "SAMNAC garlic powder" was produced, which was then used in the preparation of the food.

To make the SAMNAC garlic powder:
1. Start with 210 mL of garlic powder (100 g), which should produce approximately 290 mg of allicin when mixed with water, given that the average allicin yield from garlic powder is 2.9 mg/g (RM666.G15K6313: 93).
2. Add 15 mL of N-acetylcysteine powder (11.5 g) and blend for a few seconds to mix.
3. Add sufficient potassium bicarbonate to raise the pH to approximately 4 (3.75 mL raised the pH to 4.5) and blend for a few seconds to mix.
4. Let the mixture stand for a day at room temperature.
8. Use a food dehydrator (trays with hot air blown across them—normally used for drying fruit, vegetables, or beef jerky) to dry the fluid (I used an Excalibur). I used multiple 18-well silicone nonstick miniature donut baking molds (by Freshware) to hold the fluid, with one teaspoon of fluid in each well (approximately 65 wells total). Drying time is approximately 24 hours at 95 degrees F., followed by 36 hours at 155 degrees F.
5. Remove the "crystalized" product from the wells of the molds (approximately 102 g total).
6. Grind the crystalized product using a hand cheese grater (I used a Zyliss) to make a powder.
11. Each gram of the powder has an estimated 9.2 mg of SAMNAC (2.9 mg of allyl mercapto groups) and an estimated 110 mg of "excess" N-acetylcysteine.

To make the garlicky potatoes with bacon:
1. Cut three medium size russet potatoes into small cubes, approximately 1 cm on each side.
2. Put the cut potatoes in a pot with enough water to cover them.
3. Add one teaspoon (5 ml, 3 g) of the SAMNAC garlic powder to the pot.
4. Heat the pot to a gentle boil and cook until the potato cubes are done.
5. Cut 5 slices of bacon into pieces of approximately 1 cm by the width of the bacon slice.
6. Fry the bacon at 350 degrees F. until done.
7. Drain the potatoes.
8. Add the potatoes to the bacon in the frying pan.
9. Mix and fry until the excess water on the surface of the potato cubes is gone.
10. Serves two. The potatoes have a strong bacon flavor and a moderate garlic flavor. Each serving has up to an estimated 13 mg of SAMNAC and up to an estimated 165 mg of N-acetylcysteine.

6.2.3.4 A Nutraceutical Beverage

Garlicky tomato juice can be made by:
1. To 8 ounces of tomato juice, add one teaspoon (5 ml, 3 g) of SAMNAC garlic powder.
2. Refrigerate overnight.
3. The garlicky tomato juice has a strong tomato flavor and a moderate garlic flavor. Each serving has an estimated 27 mg of SAMNAC and an estimated 230 mg of N-acetylcysteine.

6.2.3.5 Experiments with Other Starting Ingredients

The above experiments were performed by the applicant at home using "kitchen chemistry" and naturally available sources for the thiosulfinate ingredients. Although it is not necessary for patentability to have developed a commercial scale manufacturing process (and the methods described above are sufficient for patentability), the disclosure and examples in this section illustrate experiments with some other. commercially available starting ingredients that could be used for the development of a commercial scale manufacturing process.

6.2.3.5.1 Starting with Mercaptans

A mercaptan such as allyl mercaptan could be used with N-acetylcysteine to produce the mixed disulfide S-allylmercapto-N-acetylcysteine (SAMNAC). This would require the use of an oxidizing agent to induce disulfide formation. One traditional means for doing this is by bubbling air through the reaction mixture.

Allyl mercaptan is commercially available (including food grade, which is intended for human consumption in foods) and I have used it for experiments in the past.

Allyl mercaptan is moderately dissolvable in water (5 g/L), but dissolves freely in oil, indicating that it is a lipophilic molecule. When initially added to water, it tends to float on top or cling to glassware rather than rapidly dissolving (U.S. Pat. No. 8,217,084).

Allyl mercaptan is lipophilic and will preferentially partition into the lipids of a lipid and aqueous system. The Material Safety Data Sheet for allyl mercaptan (e.g. as published by GuideChem) states that allyl mercaptan is soluble in water and also that it has a partition coefficient (Log P) of 1.51 (e.g. it equilibrates to a 30 to 1 higher concentration in the oil than in the water side of a system with both oil and water).

Propyl mercaptan has a partition coefficient (Log P) of 1.95 (e.g. it equilibrates to an almost 100 to 1 higher concentration in the oil than in the water side of a system with both oil and water).

Although allyl mercaptan (and diallyl disulfide) have lower solubility in water than in lipids, experiments have shown that their concentrations in both the membranes and the cytosol of cells in sufficient to provide biologically significant activity (U.S. Pat. No. 8,217,084).

Even a very small concentration of a mercaptan in the air is objectionable, as was evidenced in the past by the appearance of a mysterious strong odor in Manhattan on Jan. 8, 2007 that nauseated many people. Even a few well dispersed ounces of (for example) ethyl mercaptan could be enough to stink up all of Manhattan (NYTIMES2001:0121A). Although the source of the odor was not was not found, it was described as having a mercaptan-like smell and may have been a natural product produced by micro-organisms in the coastal marshes (NYTIMES2001:0121B).

Even the thought experiment of using allyl mercaptan in a bubbling mixture was enough to prevent actually doing this (in consideration of my wife and neighbors).

But for designing an industrial production process, there should be known oxidizing agents that can be used to induce disulfide formation (hydrogen peroxide comes to mind). But for my actual experiments, there is no advantage to starting with a mercaptan instead of starting with a thiosulfinate (as described in the previous sections) or a disulfide (as described below).

6.2.3.5.2 Starting with Disulfides

Figure 1A:
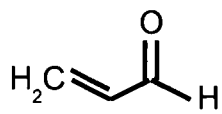
FIG. 1A through FIG. 1H show various molecules that are of interest.
Figure 1B:
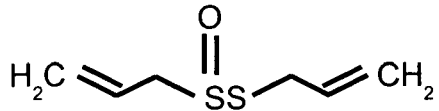
Figure 1C:
Figure 1D:
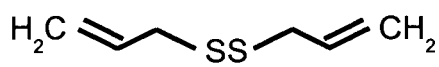
Figure 1E:
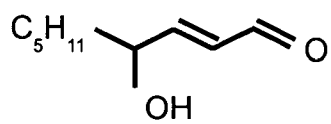
Figure 1F:
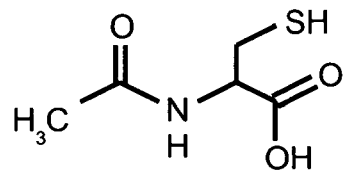
Figure 1G:
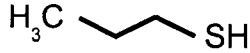
Figure 1H:
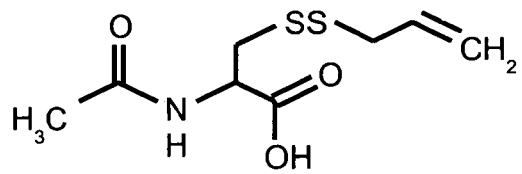
Figure 2:
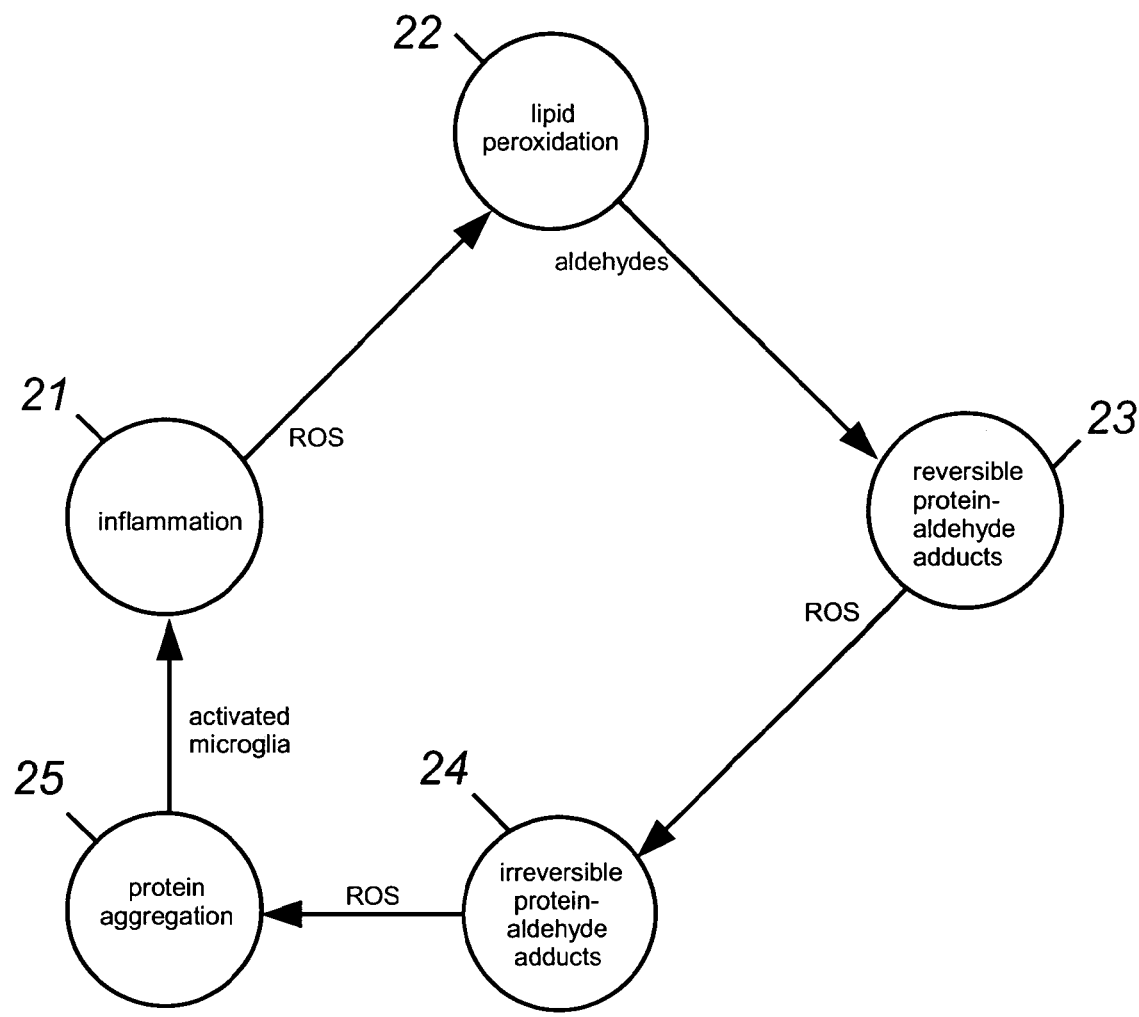
FIG. 2 shows an inflammatory feedback loop
Figure 3:
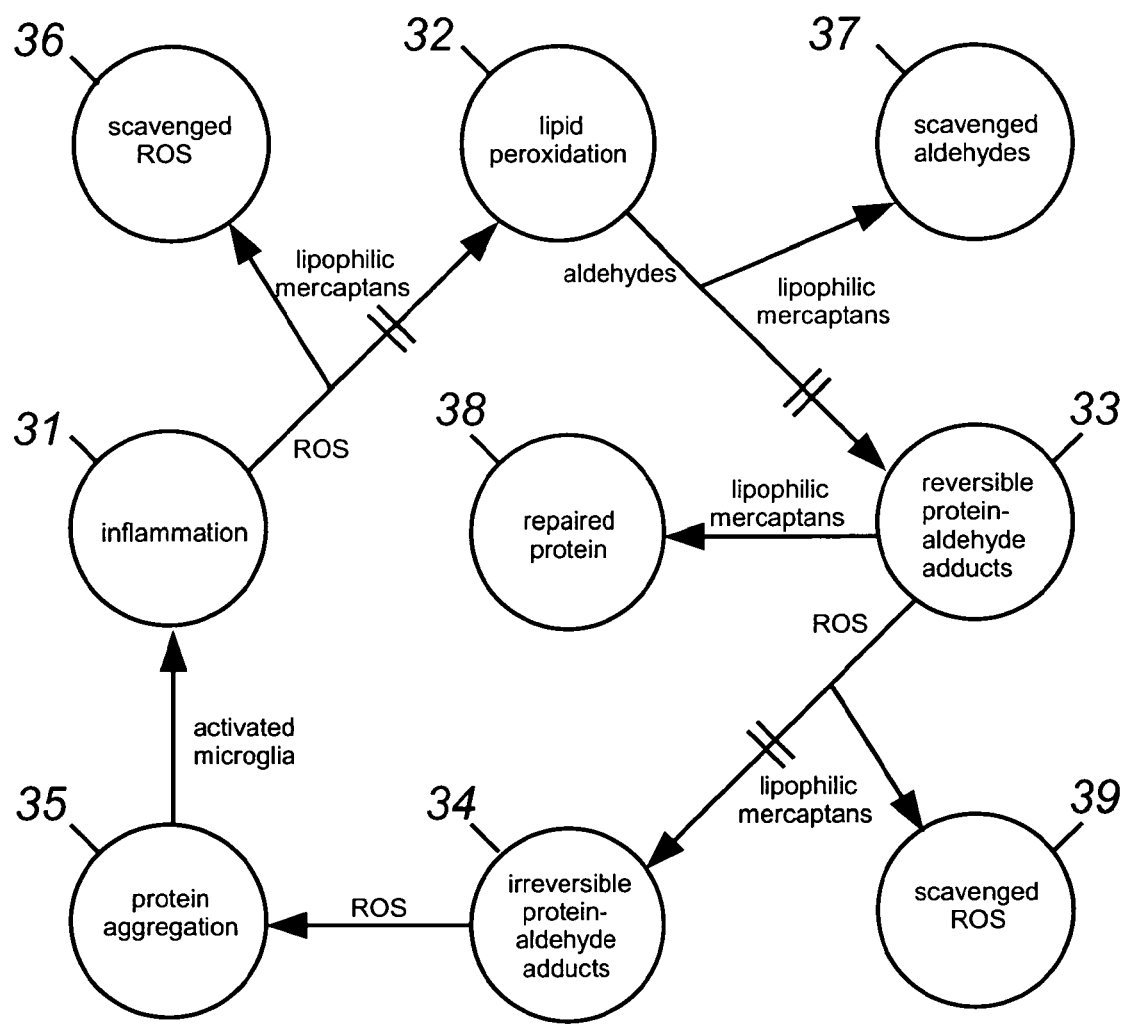
FIG. 3 shows a inflammatory feedback loop that is modified by lipophilic mercaptans.

An initial attempt to make SAMNAC powder starting with diallyl disulfide (DADS, FIG. 1D) and N-acetylcysteine was not successful, as described in this section.

A mixture of DADS and N-acetylcysteine in water produces a solution with a pH near 2, which is much to acidic for thiol-disulfide reactions to occur at a reasonable rate. An acceptable reaction rate (e.g. a speedup of 1000 times or more compared to pH=2) could be obtained at a pH of 5 or more.

The low pKa of N-acetylcysteine is due to the carboxyl group (COOH), which is normally ionized (COO$^-$) at any pH over 2. For normal cysteine, the ionized carboxyl group is "canceled out" by its ionized amino group (NH$^{3+}$) to produce a net pH near 7 when dissolved, but in N-acetylcysteine, this amino group is acetylated so its ionization is unavailable.

By adding sufficient potassium bicarbonate to the mixture (which reacts with H$^+$ to produce H$_2$O and K$^+$) the pH can be adjusted to approximately 7. (A target pH of 7 was desired because at this pH the amount of K$^+$ will be equal to the amount of SAMNAC$^-$ that is formed, which will simplify the formation of a 1:1 salt between them when the mixture is later dried.)

Note that the formed SAMNAC will be an anion in solution (the carboxyl group will remain ionized) and would be expected to form a salt with the added potassium when dried (unless the potassium is removed before drying). In this case, it is probably beneficial for the potassium to remain in the product, because potassium is safe and the potassium consumption of most people is lower than the current recommendations.

In the initial mixture, the DADS floats on the surface, but as it combines with the N-acetylcysteine, the surface layer disappears. Continuous mixing speeds up this process.

A size 0 capsule that contained the equivalent of 40 mg of allyl mercaptan and 400 mg of N-acetylcysteine (and metabolized to something near this) would have a desirable dosage of both of these ingredients. The hope was that although SAMNAC naturally is a liquid, starting with 10×N-acetylcysteine would result in 9×excess N-acetylcysteine (normally a solid), so the combination could perhaps form a solid suitable for grinding into a powder (for putting into gelatin capsules).

Because the ratio of thiols to disulfides is not changed from thiol-disulfide exchange reactions, starting with a 10×excess of N-acetylcysteine over the DADS concentration (of allyl mercaptan equivalents, with each DADS molecule counting as 2 allyl mercaptan equivalents), could be expected to produce approximately 90% retained N-acetylcysteine, 9% SAMNAC, 1% allyl mercaptan and 0.1% retained DADS (the same 10×ratio of thiols to disulfides). In practice the observation that the oily surface layer disappears implies that essentially all of the DADS and allyl mercaptan have combined with the N-acetylcysteine.

After the DADS had disappeared (not appearing on the surface of the mixture after the mixing is stopped and the mixture is allowed to settle), the mixture was dried and then ground into a powder. The result seemed to be a success.

But subsequent HPLC analysis performed as work for hire by Dr. Lawson showed that this powder did not contain a significant amount SAMNAC.

Figure 8:
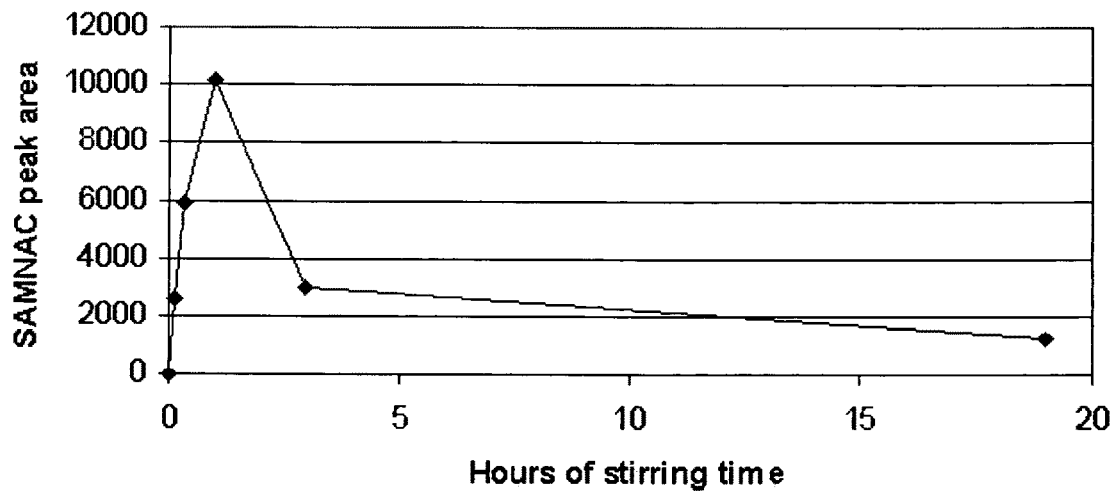
FIG. 8 shows production of SAMNAC from N-acetylcysteine and diallyl disulfide and its subsequent decline.

An experiment by Dr. Lawson showed the reason why. As shown in FIG. 8, the SAMNAC concentration in the mixture peaks at one hour (at over 90% of the theoretical maximum yield) but then declines.

In hindsight, the molecular structure of allyl mercaptan can explain this. The initial thiol-disulfide exchange reactions are rapid and complete within an hour. But there is still approximately 9×excess N-acetylcysteine in the mixture. The retained C=C double bond from the allyl mercaptan is vulnerable to a Michael addition reaction which could proceed to modify the SAMNAC molecules, decreasing the SAMNAC yield as shown.

Dr. Lawson's main conclusions were:
1. Under the above conditions, NAC and DADS rapidly react to form expected (near quantitative) amounts of SAMNAC, especially if the pH is around 5-6.
2. The instability of the formed SAMNAC can probably be corrected by lowering the pH, after SAMNAC formation to about 4-5.

Note: An easy way to lower the pH would be to use less N-acetylcysteine as a starting material (e.g. 2×excess instead of 10×), balance the pH for this amount of anion (which would take only ⅕ as much cation to do), and to then add N-acetylcysteine at the appropriate time (e.g. after one hour).

A subsequent experiment using dipropyl disulfide (which is similar to DADS but has a C—C single bond instead of the C=C double bond of DADS) was only partially successful.

Figure 9B:
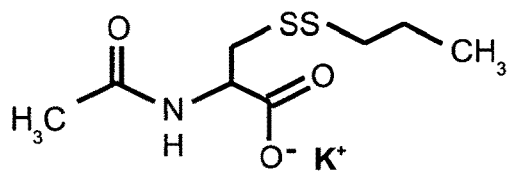
Figure 9C:
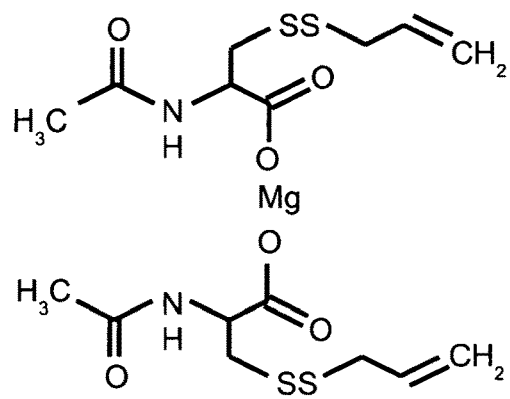
Figure 9D:
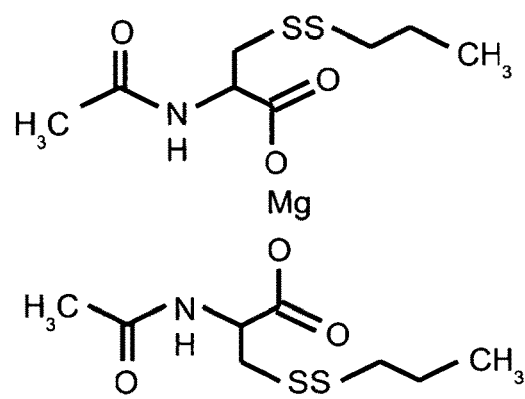
Figure 10:
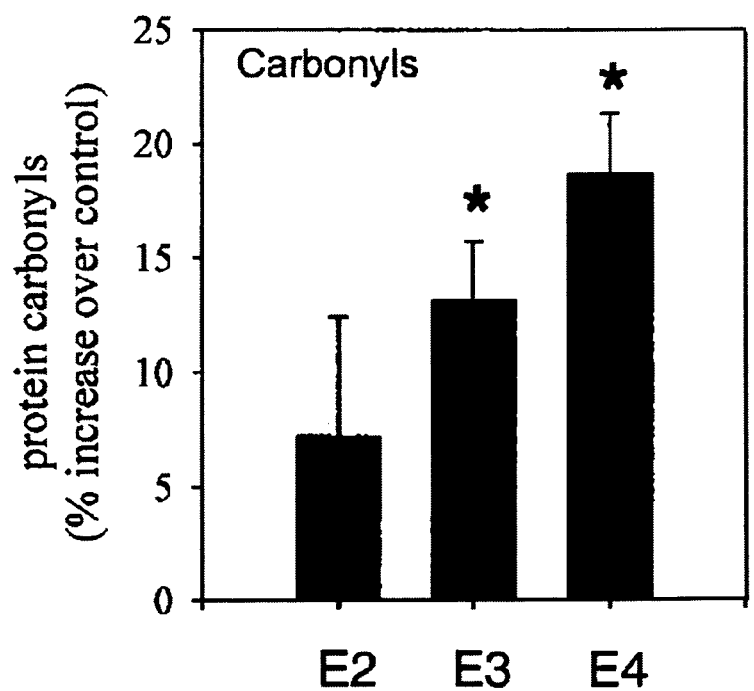
FIG. 10 (from NBA23:655) shows the effect of the APOE allele type on protein carbonyl levels.

The resulting mixture was slow to dry, and after drying soon became soft and sticky (presumably due to moisture absorption from air). Before grinding could be completed, the grinder became stuck. Also, the pile of "ground" powder "melted" together too soon to allow it to be put into capsules. So the S-propylmercapto-N-acetylcysteine salt that I made (FIG. 9B) is not suitable for putting into gelatin capsules for use as a dietary supplement and could only be be used for something else (e.g. in a nutraceutical food or beverage).

In hindsight, this may be due to the known fact that potassium salts are "highly hygroscopic" and readily absorb moisture from the atmosphere (RS403.H33:393).

Therefore, although SAMNAC could be produced from DADS and N-acetylcysteine by stopping the reaction at the appropriate point, and SPMNAC could be produced from dipropyl disulfide and N-acetylcysteine, they do not form solids when dried and would need to be used in the form of a gel capsule (with a liquid inside) to produce a dietary supplement in the form of a capsule.

6.3 Examples of Use

6.3.1 Experimental Use

It is expected that those at risk of development of a neurological disease would consume these compositions on a daily basis, either as a dietary supplement or in nutraceutical foods. Those who have developed a neurological disease are likely to consume a larger quantity as recommended or prescribed by their doctor.

Myself, some friends, and relatives have consumed these and related compounds for several years without any apparent negative effects.

In the future, similar compositions could also become available in the form of FDA approved drugs with proven safety and effectiveness for the treatment of specific diseases.

I have experimentally consumed 240 mg/day of allyl mercaptan for several weeks without any apparent negative effects (except for taste and smell unpleasantness when taking each dose!). The results of a standard comprehensive blood test at the end of the experiment were essentially normal.

6.3.2 Dosages

The anticipated viable dosage range is from a minimum of 1 mg to a maximum of 2 grams of the lipophilic mercaptan (within the composition, e.g. the mass of the lipophilic mercapto redicals within the mixed disulfide) per day. The lower end of this range encompasses unit dosages (e.g. in nutraceuticals), taking into account that multiple servings (e.g. multiple types of these nutraceuticals) could be consumed each day (e.g. for an accumulated dosage of up to 2 grams/day).

Experience with similar mercaptans has shown a dose-dependent effectiveness range of, for example, a total of 30 mg to 60 mg per day (e.g. for the treatment of chronic arsenicosis, as disclosed in U.S. Pat. No. 7,678,833). For this example, the unit dose (per capsule) was 10 mg, so the daily consumption was 3 to 6 capsules. Because arsenicosis is an extreme case, most other conditions are likely be responsive to daily dosages well below this.

The upper limit of the range is based on the dosages of mercaptans (or disulfides that metabolize to form mercaptans) that have been used in animal studies. For example, in a study of the prevention of acetaminophen poisoning in mice (PHYRES3:50), the dosage of S-allylmercaptocysteine used was up to 200 mg/kg, which would correspond to a dosage of 5000 mg of S-allylmercaptocysteine (which contains approximately 2000 mg of allyl mercaptan) fora 70 kg adult human.

The most preferred unit dosage is 25 mg of lipophilic mercaptan per unit dosage (e.g. per capsule, or per serving of a nutraceutical). Less preferred is a unit dosage within the range of 5 to 25 mg. Also less preferred is a unit dosage within the range of 25 mg to 200 mg. Even less preferred is a unit dosage within the range of 1 mg to 5 mg, or a unit dosage within the range of 200 mg to 2000 mg.

The most preferred daily dosage for healthy adults is 50 mg of lipophilic mercaptan per unit dosage (e.g. two unit doses of 25 mg each). Less preferred is a daily dosage within the range of 10 to 50 mg. Also less preferred is a daily dosage within the range of 50 mg to 200 mg. Even less preferred is a daily dosage within the range of 1 mg to 10 mg, or a daily dosage within the range of 200 mg to 2000 mg.

The most preferred daily dosage for children over age 10 is one half of the daily dosage for adults (e.g. one unit dose of 25 mg per day).

6.4 Other Lipophilic Mercaptans

The examples above have emphasized the use of lipophilic mercaptans which are present naturally in foods such as garlic, onions, and cabbage or are produced from these during normal food preparation and consumption. In particular, both allyl mercaptan and propyl mercaptan are already approved as food ingredients by the FDA. In addition, garlic oil, diallyl disulfide, onion oil, and dipropyl disulfide (which are all FDA approved for use in foods) metabolize during digestion to form allyl mercaptan or propyl mercaptan. In addition to their natural consumption by populations for millennia, these compounds have been used experimentally without apparent toxicity in animals at dosages up to 100 mg/kg, which would correspond to a dosage of 7,000 mg for a 70 kg adult human.

Because allyl mercaptan has a partition coefficient (Log P) of 1.51 (e.g. it equilibrates to a 30 to 1 higher concentration in the oil side than in the water of a system with both oil and water), the most desirable partition coefficient is approximately 1.51 (e.g. the range of 1.3 to 1.7). Propyl mercaptan has a partition coefficient (Log P) of 1.95 (e.g. it equilibrates to an almost 100 to 1 higher concentration in the oil side than in the water of a system with both oil and water) therefore a less desirable partition coefficient range is from 1.7 to 2.3 (the range which encompasses propyl mercaptan). A still less desirable partition coefficient range is from 1.0 to 1.3 (encompassing some slightly less lipophilic mercaptans) or above 2.3 (encompassing the more lipophilic mercaptans).

Therefore, the present invention is not limited to compounds where the lipophilic mercaptan component is either allyl mercaptan or propyl mercaptan. Other lipophilic mercaptans are likely to also be safe and beneficial. In particular, some control of the depth of the SH group within a lipid could be obtained by varying the carbon chain length, which may prove to be of benefit.

Because the lipophilic mercaptans can be expected to occasionally form mixed disulfides with glutathione, it is desirable to limit their molecular mass to 200 g/mol or less.

This is because if the molecular mass was greater than this, there could be the possibility that these "glutathione conjugates" would be excreted from the cell by a "multidrug resistance protein" (MRP).

Multidrug resistance proteins are also known as the "GS-X pump" because it will pump any compound "X" out of the cell provided that the "X" becomes conjugated with glutathione and provided that "X" exceeds a molecular mass of approximately 250. The GS-X pump has been extensively studied due to its role in the detoxification of various anti-tumor chemotherapeutic drugs, such as Cisplatin (whose molecular mass is 301 g/mol), thereby reducing their effectiveness (QP606.G59G59:199). Tumor cells with increased expression of the GS-X pump are termed "multi-drug resistant".

Another consideration is that many molecular receptors respond selectively to various organic ring structures. In order to avoid the unintentional recognition of the lipophilic mercaptan by some type of receptor (e.g. an untended side effect), it is desirable to not include any ring structures in the structure of the lipophilic mercaptan.

The most preferred lipophilic mercaptans are allyl mercaptan and propyl mercaptan, because both of these (and their respective disulfides) are already approved by the FDA for use in foods. Because they both have a carbon backbone of 3 carbon atoms, the most preferred number of carbon atoms is 3. Carbon backbones in the range of 1 to 2 are less preferred. Carbon backbones in the range of 4 to 5 are also less preferred. Carbon backbones of length 6 and above are even less preferred.

In general, any lipophilic mercaptans of the invention should be an organic molecule (i.e. include a backbone of carbon and also include hydrogen atoms along with the other atoms in the molecule), the carbon backbone can be branched, but it cannot have any rings. In other words, the molecule must have a single SH group, optionally have other groups attached to the carbon backbone (branching is not excluded), and have a molecular mass of 200 g/mol or less.

6.5 Other Neurodegenerative Diseases

Although this disclosure has focused on Alzheimer's and Parkinson's diseases, those skilled in the art will recognize that various other neurodegenerative diseases share the features of neuroinflammation, lipid peroxidation, increased levels of protein carbonyls, and in many cases various types of protein aggregation. These are all indicators that aldehydes are being formed as lipid peroxidation products, and that there are protein-aldehyde adducts being formed. One of skill in the art will recognize that the present invention will be useful in limiting disease progression for all of the diseases that share these characteristics.

6.5.1 Lewy Body Disease

Lewy body disease is very similar to Parkinson's disease and is sometimes considered to be a less advanced form of Parkinson's disease. In particular, it exhibits excessive formation of Lewy bodies (protein aggregates composed largely of alpha syneuclein, as described in the disclosure above). The present invention can be used to decrease the formation of Lewy bodies for this disease, just as it can for Parkinson's disease.

6.5.2 Tauopathys

Taupathies are a class of neurodegenerative diseases associated with the pathological aggregation of tau protein in the human brain. The current invention can decrease the amount of protein aggregation in the neurofibrillary tangles of tauopathies, just as it can in Alzheimer's disease.

6.5.3 Multiple Sclerosis

In mice with Experimental Autoimmune Enchephalomyelitis (EAE, an animal model for multiple sclerosis) the autoinflammation induced demyelination of the myelin sheath of neurons can be decreased by 80% by treatment with the aldehyde scavenger hydralazine (NEURO173:150). This treatment also delayed the age of onset of the disease by 30% and reduced the "EAE behavioral score" by 50%. These results indicate that aldehyde scavenging by lipophilic mercaptans will protect against the development and progression of multiple sclerosis.

Note: Hydralazine is a small molecule with an exposed amino group that can "compete" with the amino groups of proteins for damage from acrolein. (Each hydralazine-aldehyde adduct is "a protein-aldehyde adduct that didn't happen".) In order to be effective, it needs to be used in a high concentration (the competition between the amino groups of hydalazine and those of proteins is in a level playing field). At these concentrations, hydalazine has toxic side effects, so it hasn't been used for this purpose in humans. Still, the experimental results in mice indicate that lipophilic mercaptans will work in humans.

6.5.4 Polyneuropathy

Polyneuropathy also involves the destruction of the myelin sheath of neurons, most commonly due to an autoimmune response. In this respect it is even more similar to EAE than Multiple Sclerosis, so the results reported for suppression of EAE in mice (NEUR0173:150, described in the previous section) indicate that lipophilic mercaptans will protect against the development and progression of polyneuropathy.

6.5.5 Spinal Cord Injury

It is well established that the overall pathophysiology of spinal cord injure consists on an initial primary insult, which is characterized by mechanical injury, as well as a number of secondary injuries, which are largely mediated by biochemical mechanisms and oxidative stress. The spinal cord continues to degenerate following the initial insult, and the lesion spreads to adjacent, otherwise uninjured tissues. A study using guinea pigs has shown that subsequent to the injury, the level of protein-acrolein adducts increases by almost 500%. This could induce a feedback cycle involving neuroinflammation which then drives the spreading of the lesion.

6.5.6 Ischemia

It is also well established that most of the neurotoxicity from ischemia cones not from the period of deprivation of oxygen, but rather from the reperfusion and subsequent persistent neuroinflammation.

Evidence for such a feed back loop is the involvement of NFkB activation and the protective effect of its inhibition (FOLIABIOL53:164).

Further evidence for the involvement of an inflammation to aldehyde to inflammation feedback loop is elevation of HNE that occurs, and the protective effect of treatment with edaravone (STROKE36:2220).

These results indicate that lipophilic mercaptans should be effective for the treatment of ischemia.

6.5.7 Stroke

Because stroke is primarily involves ischemia in its pathogenesis, stroke treatment would also benefit from the suppression of the inflammatory feedback loop.

Therefore, lipophilic mercaptans should be effective for the treatment of stroke.

7. Recent Developments

The unsuccessful attempts to form a solid composition containing SAMNAC or SPMNAC that could be ground into a powder for use in dietary supplements (described in section 6.2.3.5.2 above) have been also described in the parent application (Ser. No. 13/373,878 which was filed on Dec. 5, 2011). Subsequent to the filing of the parent application, the applicant has discovered ways to make the desired compositions, as disclosed and taught below.

7.1 A Successful Dietary Supplement Capsule Composition

By using calcium carbonate to adjust the pH (instead of potassium bicarbonate), a calcium salt is formed (instead of a potassium salt), which forms a solid which can easily be ground into a powder suitable for use in a capsule.

The procedure I used is:

1. Mix 250 mL (177 g) of N-acetylcysteine and 80 mL (19.5 g) of calcium carbonate dissolved in one liter of distilled water (the resulting pH is approximately 5.8).
2. Add 80 mL (78 g) of onion oil (a "natural" source of dipropyl disulfide and various propyl mixed sulfides, adding up to approximately 37% propylmercapto groups by weight).
3. Mix for 24 hours (in air)
4. Use a food dehydrator (trays with hot air blown across them—normally used for drying fruit, vegetables, or beef jerky) to dry the fluid (I used an Excalibur). I used multiple 18-well silicone nonstick miniature donut baking molds (by Freshware) to hold the mixture, with one tablespoon of fluid in each well (approximately 144 wells total). Drying time is approximately 24 hours at 95 degrees F., followed by 36 hours at 155 degrees F.
5. Remove the hardened product from the wells of the molds (approximately 345 g total).
6. Grind the hardened product using a hand cheese grater (I used a Zyliss) to make a white powder.
7. Use a capsule filler to fill approximately 1000 size "0" capsules (I used Cap-M-Quik).

Each capsule has an estimated to have a maximum of 63 mg of S-propylmercapto-N-acetylcysteine (which gives 20 mg of propylmercapto groups) and approximately 140 mg of "excess" N-acetylcysteine.

7.2 Additional Compositions

7.2.1 A Higher Dosage Capsule

1. Mix 120 ml (85 g) of N-acetylcysteine and 180 mL (7.5 g) of magnesium carbonate dissolved in one liter of distilled water (the resulting pH is approximately 7).
2. Add 45 mL (43 g) of garlic oil (a "natural" source of diallyl disulfide and various allyl mixed sulfides, adding up to approximately 60% allylmercapto groups by weight).
3. Mix for 1 hour (in air).
4. Use a food dehydrator (trays with hot air blown across them—normally used for drying fruit, vegetables, or beef jerky) to dry the fluid (I used an Excalibur). I used multiple 18-well silicone nonstick miniature donut baking molds (by Freshware) to hold the mixture, with one tablespoon of fluid in each well (approximately 144 wells total). Dry for 44 hours at 52 degrees C.
5. Remove the hardened product from the wells of the molds.
6. Grind the hardened product using a hand cheese grater (I used a Zyliss) to make a white powder.
7. Use a capsule filler to fill approximately 500 size "0" capsules (I used Cap-M-Quik).

Each capsule has an estimated to have a maximum of 160 mg of S-allylmercapto-N-acetylcysteine (which gives 50 mg of allyl mercapto groups) and 50 mg of excess N-acetylcysteine. This formulation is optimized to have close to a 1 to 1 ratio between the number of allylmercapto groups and the number of N-acetylcysteine molecules in the ingredients, producing a higher dosage of lipophilic mercaptan (i.e. 50 mg) in each capsule.

7.2.2 A Whey Protein Based Capsule

1. Mix 125 ml (89 g) of N-acetylcysteine and 480 mL (17 g) of magnesium carbonate dissolved in one liter of distilled water (the resulting pH is approximately 6).
2. Add 45 mL (43 g) of garlic oil (a "natural" source of diallyl disulfide and various allyl mixed sulfides, adding up to approximately 60% allylmercapto groups by weight).
3. Mix for 1 hour (in air).
4. Use a food dehydrator (trays with hot air blown across them—normally used for drying fruit, vegetables, or beef jerky) to dry the fluid (I used, an Excalibur). I used multiple 18-well silicone nonstick miniature donut baking molds (by Freshware) to hold the mixture, with one tablespoon of fluid in each well (approximately 144 wells total). Dry for 48 hours at 35 degrees C.
5. Remove the hardened product from the wells of the molds.
6. Grind the hardened product using a hand cheese grater (I used a Zyliss) to make a white powder.
7. Use a capsule filler to fill approximately 1000 size "0" capsules (I used Cap-M-Quik).

Each capsule has an estimated to have a maximum of 80 mg of S-allylmercapto-N-acetylcysteine (which gives 25 mg of allyl mercapto groups) and 25 mg of excess N-acetylcysteine. This formulation is optimized to have close to a 1 to 1 ratio between the number of allylmercapto groups and the number of N-acetylcysteine molecules in the ingredients, to include a higher amount of magnesium (a mineral which is commonly deficient in modern diets), and to include whey protein.

7.2.3 A Rice Protein Based Capsule

1. Mix 125 ml (89 g) of N-acetylcysteine and 180 mL (7 g) of magnesium carbonate dissolved in one liter of distilled water (the resulting pH is approximately 6).
2. Add 45 mL (43 g) of garlic oil (a "natural" source of diallyl disulfide and various allyl mixed sulfides, adding up to approximately 60% allylmercapto groups by weight).
3. Mix for 1 hour (in air).
4. Use a food dehydrator (trays with hot air blown across them—normally used for drying fruit, vegetables, or beef jerky) to dry the fluid (I used an Excalibur). I used multiple 18-well silicone nonstick miniature donut baking molds (by Freshware) to hold the mixture, with one tablespoon of fluid in each well (approximately 144 wells total). Dry for 48 hours at 35 degrees C.
5. Remove the hardened product from the wells of the molds.
6. Grind the hardened product using a hand cheese grater (I used a Zyliss) to make a white powder.
7. Use a capsule filler to fill approximately 1000 size "0" capsules (I used Cap-M-Quik).

Each capsule has an estimated to have a maximum of 80 mg of S-allylmercapto-N-acetylcysteine (which gives 25 mg of allyl mercapto groups) and 25 mg of excess N-acetylcysteine. This formulation is optimized to have close to a 1 to 1 ratio between the number of allylmercapto groups, the number of N-acetylcysteine molecules, and divalent magnesium bonds available for salt formation in the ingredients, to include a higher amount of magnesium (a mineral which is commonly deficient in modern diets), and to use rice protein (because some people avoid whey protein).

These examples are illustrative and the invention is not intended to be limited to these examples.

What is claimed is:

1. A method of decreasing protein-aldehyde adducts in a human diagnosed with Parkinson's Disease, said method comprising:
    administering to the human an organosulfur composition comprising an effective amount of a mixed disulfide of a lipophilic mercaptan disulfide bonded to N-acetylcysteine, wherein the mixed disulfide is bonded as a two to one salt with a divalent cation; said lipophilic mercaptan selected from the group consisting of propyl mercaptan, propenyl mercaptan, and allyl mercaptan;
    wherein said lipophilic mercaptan reacts with an aldehyde within the lipid membranes of said human, said aldehyde being in the form of an aldehyde or in the form of a protein-aldehyde adduct, to produce a molecular conjugate of said lipophilic mercaptan and said aldehyde;
    thereby decreasing protein-aldehyde adducts in the human.

2. The method of claim 1 where said administration of said organosulfur composition produces a decrease in the amount of protein carbonyls within the frontal cortex region of the brain.

3. The method of claim 1 where said administration of said organosulfur composition produces a decrease in the amount of protein carbonyls within the substantia nigra region of the brain.

4. The method of claim 1 where said organosulfur composition is a drug.

5. The method of claim 4 where the disulfide bonded lipophilic mercaptan within said organosulfur composition is administered orally in an amount within the range of 1 mg to 2,000 mg per day.

6. The method of claim 1 where said organosulfur composition is a nutraceutical.

7. The method of claim 6 where the disulfide bonded lipophilic mercaptan is propyl mercaptan.

8. The method of claim 6 where the disulfide bonded lipophilic mercaptan is allyl mercaptan.

9. The method of claim 6 where the unit dosage of the disulfide bonded lipophilic mercaptan within said organosulfur composition is within the range of 1 mg to 200 mg.

10. The method of claim 1 where said organosulfur composition is a dietary supplement.

11. The method of claim 10 where the disulfide bonded lipophilic mercaptan is propyl mercaptan.

12. The method of claim 10 where the disulfide bonded lipophilic mercaptan is allyl mercaptan.

13. The method of claim 10 where the unit dosage of the disulfide bonded lipophilic mercaptan within said organosulfur composition is within the range of 1 mg to 200 mg.

14. The method of claim 1 where the protein is alpha-synuclein.

* * * * *